(12) United States Patent
Rivron et al.

(10) Patent No.: US 9,822,336 B2
(45) Date of Patent: Nov. 21, 2017

(54) BLASTOID, CELL LINE BASED ARTIFICIAL BLASTOCYST

(71) Applicants: Universiteit Maastricht, Maastricht (NL); KONINKLIJKE NEDERLANDSE AKADEMIE VAN WETENSCHAPPEN, Amsterdam (NL)

(72) Inventors: Nicolas Clément Rivron, Juvisy sur orge (FR); Clemens Antoni Van Blitterswijk, Ruigahuizen (NL); Niels Geijsen, Bilthoven (NL); Erik Jacob Vrij, Maastricht (NL)

(73) Assignees: UNIVERSITEIT MAASTRICHT, Maastricht (NL); KONINKLIJKE NEDERLANDSE AKADEMIE VAN WETENSCHAPPEN, Amsterdam (NL)

( * ) Notice: Subject to any disclaimer, the term of this patent is extended or adjusted under 35 U.S.C. 154(b) by 0 days.

(21) Appl. No.: 14/784,659

(22) PCT Filed: Apr. 16, 2014

(86) PCT No.: PCT/NL2014/050239
§ 371 (c)(1),
(2) Date: Oct. 15, 2015

(87) PCT Pub. No.: WO2014/171824
PCT Pub. Date: Oct. 23, 2014

(65) Prior Publication Data
US 2016/0060593 A1 Mar. 3, 2016

(30) Foreign Application Priority Data

Apr. 16, 2013 (EP) .................................... 13164018

(51) Int. Cl.
| | |
|---|---|
| C12N 5/00 | (2006.01) |
| C12N 5/073 | (2010.01) |
| A01K 67/027 | (2006.01) |
| C12N 5/071 | (2010.01) |
| C12N 15/873 | (2010.01) |
| A61B 17/435 | (2006.01) |

(52) U.S. Cl.
CPC .......... *C12N 5/0603* (2013.01); *A01K 67/027* (2013.01); *A61B 17/435* (2013.01); *C12N 5/0604* (2013.01); *C12N 5/0697* (2013.01); *C12N 15/873* (2013.01); *A01K 2227/105* (2013.01); *A01K 2267/02* (2013.01); *C12N 2500/44* (2013.01); *C12N 2501/01* (2013.01); *C12N 2501/105* (2013.01); *C12N 2501/119* (2013.01); *C12N 2501/15* (2013.01); *C12N 2501/16* (2013.01); *C12N 2501/235* (2013.01); *C12N 2501/392* (2013.01); *C12N 2501/415* (2013.01); *C12N 2501/727* (2013.01); *C12N 2501/91* (2013.01); *C12N 2502/02* (2013.01); *C12N 2502/025* (2013.01); *C12N 2517/00* (2013.01); *C12N 2531/00* (2013.01); *C12N 2535/00* (2013.01)

(58) Field of Classification Search
None
See application file for complete search history.

(56) References Cited

U.S. PATENT DOCUMENTS

| | | |
|---|---|---|
| 2006/0085866 A1 | 4/2006 | Poueymirou et al. |
| 2008/0028479 A1 | 1/2008 | Poueymirou et al. |
| 2008/0078000 A1 | 3/2008 | Poueymirou et al. |
| 2008/0078001 A1 | 3/2008 | Poueymirou et al. |

(Continued)

FOREIGN PATENT DOCUMENTS

| | | |
|---|---|---|
| EP | 2088191 A1 | 8/2009 |
| WO | 2006044962 A1 | 4/2006 |

(Continued)

OTHER PUBLICATIONS

Aikawa et al. J Biosci Bioengin Mar. 2014;117:358-65, ePub Oct. 7, 2013.*
Nagy et al. Methods in Enzymol 2010;476:124-49.*
Wang et al. Mech Develop 1997;62:137-45.*
Summers, J Assist Reprod Genet 2013;30:995-9.*
Zhang et al. In Vitro Dev Biol.—Animal 2012;48:30-36.*
Wang et al. Dev Biol 2004;275:192-201.*
Stachelscheid et al. J Tis Engineer Regenerat Med 2013;7:729-41.*
Draper et al. Curr Opin Obstet Gynecol 2002;14:309-315.*
Mullins et al. Journal of Clinical Investigation, 1996.*

(Continued)

*Primary Examiner* — Janice Li
(74) *Attorney, Agent, or Firm* — TraskBritt, P.C.

(57) ABSTRACT

A method for making an at least double layered cell aggregate and/or an artificial blastocyst, and/or a further-developed blastoid termed blastoid, by forming a double layered cell aggregate from at least one trophoblast cell and at least one pluripotent and/or totipotent cell, and culturing the aggregate to obtain an artificial blastocyst having a trophectoderm-like tissue that surrounds a blastocoel and an inner cell mass-like tissue. The cell aggregate can be formed from toti- or pluripotent stem cell types, or induced pluripotent stem cell types, in combination with trophoblast stem cells. Formation of a blastoid can be achieved by culturing the cell aggregate in a medium preferably comprising one or more of a Rho/ROCK inhibitor, a Wnt pathway modulator, a PKA pathway modulator, a PKC pathway modulator, a MAPK pathway modulator, a STAT pathway modulator, an Akt pathway modulator, a Tgf pathway modulator and a Hippo pathway modulator. Also, a method for growing an at least double layered cell aggregate into an artificial blastocyst, and into a further-developed blastoid, a foetus or a live animal and an in vitro cell culture comprising the mentioned compounds and/or cell aggregates.

9 Claims, 4 Drawing Sheets

(56) References Cited

U.S. PATENT DOCUMENTS

| | | | | |
|---|---|---|---|---|
| 2010/0240132 A1* | 9/2010 | Lanza | ............... | A01K 67/0273 435/455 |
| 2012/0009645 A1 | 1/2012 | Oh et al. | | |
| 2012/0192299 A1 | 7/2012 | Kim | | |

FOREIGN PATENT DOCUMENTS

| | | |
|---|---|---|
| WO | 2010107392 A1 | 9/2010 |
| WO | 2012117968 A1 | 9/2012 |
| WO | 2014171824 A1 | 10/2014 |

OTHER PUBLICATIONS

Moreadith et al., J. Mol. Med., 1997;75:208-16.*
Pera et al. Journal of Cell Science 2000; 113: 5-10.*
Akagi et al. J Reprod Dev 2010;56:475-9.*
PCT International Preliminary Report on Patentability, PCT/NL2014/050239 dated Oct. 20, 2015.
Obokata H, Sasai Y, Niwa H, Kadota M, Andrabi M, Takata N, Tokoro M, Terashita Y, Yonemura S, Vacanti CA, Wakayama T., Bidirectional developmental potential in reprogrammed cells with acquired pluripotency., Nature. Jan. 30, 2014;505(7485):676-80. doi: 10.1038/nature12969.
Macfarlan TS, Gifford WD, Driscoll S, Lettieri K, Rowe HM, Bonanomi D, Firth A, Singer O, Trono D, Pfaff SL, Embryonic stem cell potency fluctuates with endogenous retrovirus activity, Nature, Jul. 5, 2012; 487 (7405): 57-63; doi: 10.1038/nature11244.
Chen G, Gulbranson DR, Hou Z, Bolin JM, Ruotti V, Probasco MD, Smuga-Otto K, Howden SE, Diol NR, Propson NE, Wagner R, Lee GO, Antosiewicz-Bourget J, Teng JM, Thomson JA., "Chemically defined conditions for human iPSC derivation and culture," Nat. Methods. 2011.
Buehr et al., Capture of Authentic Embryonic Stem Cells from Rat Blastocysts, Cell, Dec. 26, 2008, pp. 1287-1298, vol. 135, No. 7.
Chen, et al., Development of Mouse Embryos in vitro: Preimplantation to the Limb Bud Stage, Science, New Series, Abstract, vol. 218, No. 4567, Oct. 1, 1982, pp. 66-68.
O, Peitz M, Hemberger M, Schorle H. Derivation and Maintenance of Murine Trophoblast Stem Cells under Defined Conditions. Stem Cell Reports., Jan. 30;2(2):232-42. doi: 10.1016/j.stemcr.2013.12.013. e, Collection Feb. 11, 2014.
Morgani SM, Canham MA, Nichols J, Sharov AA, Migueles RP, Ko MS, Brickman JM. Totipotent embryonic stem cells arise in ground-state culture conditions. Cell Rep. Jun. 27, 2013;3(6):1945-57. doi: 10.1016/j.celrep.2013.04.034. Epub Jun. 6, 2013.
Huang et al., Efficient Production of Mice from Embryonic Stem Cells Injected into Four- or Eight-Cell Embryos by Piezo Micromanipulation, Stem Cells, Jul. 2008, pp. 1883-1890, vol. 26, No. 7.
Obokata et al., Retraction: Bidirectional development potential in reprogrammed cells with acquired pluripotency, Nature, Jul. 2, 2014, p. 112, vol. 551, No. 7507.
Rivron et al., Tissue deformation spatially modulates VEGF signaling and angiogenesis, Proceedings of the National Academy of Sciences, May 1, 2012, pp. 6886-6891, vol. 109, No. 18.
Eggan et al., Hybrid vigor, fetal overgrowth, and viability of mice derived by nuclear cloning and tetraploid embryo complementation, Proceedings of the National Academy of Sciences, May 22, 2011, pp. 6209-6214, vol. 98, No. 11.
Nagy et al., Derivation of completely cell culture-derived mice from early-passage embryonic stem cells, Proceedings of the National Academy of Sciences, Sep. 15, 1993, pp. 8424-8428, vol. 90, No. 18.
PCT International Written Opinion, PCT/NL2014/050239, dated Jul. 30, 2014.
PCT International Search Report, PCT/NL2014/050239, dated Jul. 30, 2014.

* cited by examiner

BLASTOID, CELL LINE BASED ARTIFICIAL BLASTOCYST

CROSS-REFERENCE TO RELATED APPLICATIONS

This application is a national phase entry under 35 U.S.C. §371 of International Patent Application PCT/NL2014/050239, filed Apr. 16, 2014, designating the United States of America and published in English as International Patent Publication WO 2014/171824 A1 on Oct. 23, 2014, which claims the benefit under Article 8 of the Patent Cooperation Treaty and under 35 U.S.C. §119(e) to European Patent Application Serial No. 13164018.7, filed Apr. 16, 2013, the disclosure of each of which is hereby incorporated herein in its entirety by this reference.

FIELD

The invention is in the field of life sciences.

INTRODUCTION

Stem cells can proliferate, differentiate and organize into any embryonic and adult organs and tissues. As such, they are of major importance for medicine.

Stem cells can be obtained by harvesting them from an embryonic structure, for instance a blastocyst. This requires sacrificing pregnant animals. In addition, harvesting stem cells from embryos disrupts the embryonic structure from which they are harvested and usually prevents this structure from becoming a live animal. Also, stem cells can sometimes be obtained from an adult animal by extraction of suitable tissue.

Alternatively, stem cells can be obtained from differentiated cells, by a process called cellular reprogramming. Cellular reprogramming increases the potency of a cell. Thus it is possible to create stem cells from many different cell types, such as for instance skin cells. Reprogrammed stem cells are similar to stem cells, in that they have the capability to differentiate into embryonic and/or extraembryonic tissue.

Stem cells can be proliferated ("cultured") indefinitely in vitro while retaining their pluripotency and differentiation potential. This way, stem cells can be multiplied, genetically manipulated and stored, allowing the use of batches of the cells, for instance for research purposes. Such cells descendent from a single cell or a small number of cells and kept alive is called a cell line. A cell line is thus essentially genetically homogeneous.

Some stem cells have the capability to differentiate into embryonic or extra-embryonic tissue. For example, an embryonic stem cell ("ES-cell") has the capability to mostly differentiate into the embryo proper and some extra-embryonic tissues, for example, the yolk sac while a trophoblast stem cell ("TS-cell") has the capability to mostly differentiate into extra-embryonic tissue, such as placental tissues. Both ES-cells and TS-cells are therefore considered pluripotent stem cells.

Also, stem cells exist that are capable of differentiating into any tissue, among which both embryonic and extraembryonic tissues. Such stem cells are called totipotent (or sometimes omnipotent). Three classical examples are: Macfarlan T S, Gifford W D, Driscoll S, Lettieri K, Rowe H M, Bonanomi D, Firth A, Singer O, Trono D, Pfaff S L, Embryonic stem cell potency fluctuates with endogenous retrovirus activity Nature 2012 Jul. 5; 487 (7405): 57-63; doi: 10.1038/nature11244;

Morgani S M, Canham M A, Nichols J, Sharov A A, Migueles R P, Ko M S, Brickman J M, Totipotent embryonic stem cells arise in ground-state culture conditions. Cell Rep. 2013 Jun. 27; 3(6):1945-57. doi: 10.1016/j.celrep.2013.04.034. Epub 2013 Jun. 6.)

Bidirectional developmental potential in reprogrammed cells with acquired pluripotency. Obokata H, Sasai Y, Niwa H, Kadota M, Andrabi M, Takata N, Tokoro M, Terashita Y, Yonemura S, Vacanti C A, Wakayama T. Nature. 2014 Jan. 30; 505(7485):676-80. doi: 10.1038/nature12969.

Embryonic stem cells can be used to create genetically modified species. This is done by combining a stem cell and an embryonic structure which was naturally formed and subsequently harvested from a pregnant mother. The natural embryonic structure is usually a morula or a blastocyst. The combined embryonic stem cells and embryonic structure are placed in the uterus of a foster mother in order to develop and form an animal. Thus, both the cells naturally present in the embryonic structure and the injected embryonic stem cell(s) grow together into one embryo and subsequently an adult animal. This results in an animal with two distinct genetic profiles: one profile issued from the embryo and one profile issued from the added embryonic stem cells. Thus, natural embryonic structures such as blastocysts are used as a vehicle to support the development of the stem cells: there is no in vitro formation of a blastocyst or of a double-layered cells structure. The resulting embryo further develops in vivo to result, after birth, in a live animal with tissues originating from the natural morula/blastocyst, as well as with tissues originating from the combined cells, and therefore has two distinct genetic profiles.

An animal with two distinct genetic profiles is called a chimera. Chimeras obtained by combining genetically modified stem cells and a natural morula or blastocyst are used to form genetically modified species. This can be achieved by selecting which animals include the genetic modification, and discarding those that do not, and subsequent breeding of the selected animals until the genetic modification is uniformly present in all animals of the strain.

This way of obtaining genetically modified organisms is lengthy, difficult and laborious due to the breeding programme that is required to obtain a strain of live animals with the same modification. In addition, it requires the killing of numerous animals either to harvest natural morula/blastocysts or to select the appropriate chimeric pups.

Embryonic stem cells can also be combined with a tetraploid embryonic structure. A tetraploid embryonic structure is formed by fusing the two cells from a 2-cell-stage embryonic structure obtained by harvesting from a pregnant female. The resulting single cell has lost the capability to form an inner cell mass and embryo. Thus, upon implantation into a uterus, a tetraploid embryonic structure can form a placenta but not an embryo. A tetraploid embryonic structure can, however, be complemented in vitro with embryonic stem cells. The resulting embryonic structure can be inserted in a uterus, where it grows into a further-developed embryo. Because the tetraploid cells only form the extraembryonic tissue, the added embryonic stem cells form the totality of the embryo.

This so called tetraploid complementation technique thus allows forming genetically modified species while avoiding the intermediate step of chimera formation.

The resulting genetically modified animal strains, either obtained by chimera breeding or by the tetraploid complementation technique, are among others used to understand development and diseases.

However, the formation of an animal using the tetraploid complementation still requires a natural vehicle harvested from a pregnant female, such as a 2 cell-stage embryonic structure, and is thus limited by the availability of such a vehicle.

Embryoid bodies ("EB") are used to study and obtain differentiated tissue from embryonic stem cells. Embryoid bodies are multicellular spheres of 200 to 4000 μm in diameter obtained via aggregation of embryonic stem cells. This is commonly achieved by resuspending ES-cells (i.e. 2000 cells) in a hanging drop (a drop hanging from the plastic cover of a dish) in culture medium. Upon implantation into an animal or upon further in vitro culture, EBs differentiate and form multiple non-pluripotent cell types but do not organize into an organism. EB culture and implantation allow for the assessment of the differentiation potential of a cell line or to trigger the differentiation of ES cells as an intermediate step toward the formation of more differentiated cell types. Embryoid bodies formed using ES cells can hitherto not form a blastocyst or placental tissues, and therefore they cannot be used to obtain an embryo or a live animal.

In vitro fertilisation involves the in vitro combination of mammalian gametes. A gamete is a germ cell with only has half a chromosome set (a haploid cell). Upon fusion of a female gamete (an oocyte) and a male gamete (a sperm), both the two half sets of chromosomes combine to form the first diploid cell, the zygote. The in vitro generated zygote is subsequently transferred to a uterus.

Thus, this method makes use of the fusion of primary germ cells to obtain a cell that differentiates naturally to form a live blastocyst.

EP 2 088 191 describes the formation of iBLASTs, which form a trophecoderm by genetically modifying ES-cells to express cdx2. A disadvantage of this technique is that an embryo which forms from this technique may inadvertently incorporate DNA from modified $ES^{TSi}$ cells, thus contaminating the genetic profile of an organism obtained therefrom.

Embryos are valuable to assess the potential of a drug or the toxicity of a substance on embryonic development. In addition, they are valuable to observe tissue differentiation, proliferation and organization. With this aim, a blastocyst or other embryonic cell structure harvested from a pregnant animal can be cultured in vitro, leading to a further developed embryo. This among others allows for the study and assessment of (i) cell differentiation, tissue development and regeneration, (ii) the effect of a substance on such processes as differentiation, development and regeneration, (iii) the toxicity of a substance. However, such investigations prevent the embryonic structure from becoming a live animal and require sacrificing the mother animals used for the generation of the embryos.

Currently, the efficacy and safety of preclinical drug discovery is hampered by a lack of relevant in vitro models. For example, the European Center for the Validation of Alternative Methods (ECVAM) currently uses the embryonic stem cell test (EST) which makes use of the differentiation of EB's into a single differentiated cell type (i.e. cardiomyocites). This assay poorly reflects the toxicity of a substance on other tissues and organs.

The processes of (i) generation of genetically modified species, (ii) development of drugs, (iii) assessment of toxicity are laborious and require the sacrifice of numerous pregnant mammalians, the consumption of important resources (space, feed, work) and high legal requirements. This invention presents the formation of artificial blastocysts using cell lines as an alternative to the use of embryos harvested from pregnant animals.

SUMMARY OF THE INVENTION

The present invention provides a method to promote the organization of cells from cell lines into a double-layered cell aggregate, and subsequently in an artificial blastocyst. This artificial blastocyst can be grown further either in vivo or in vitro. The term "blastoid" refers to an embryonic structure which includes the post-cavitation artificial blastocyst (the cavitated artificial blastocyst) and further developed embryos, descendent from an artificial blastocyst, up until formation of the fetus.

Because a stem cell line can be multiplied almost indefinitely, the present method for forming an artificial blastocyst generally circumvents the ethical and practical problems associated with the requirement of in vivo generation and harvesting embryos from a pregnant mother. Large numbers of blastoids can be generated, which is currently not possible by other means. This method also allows for simplified access to genetically-modified or non-genetically-modified embryos or tissues, descendent from the artificial blastocyst. The method also allows for the formation of embryos and organisms by combining several cell lines of similar or different species.

The present invention provides an in vitro method of making an at least double layered cell aggregate or a blastoid comprising the steps of:
  forming an initial cell aggregate by combining at least one trophoblast cell and at least one pluripotent and/or totipotent cell;
  culturing said initial cell aggregate in a culture medium to obtain an at least double layered cell aggregate comprising an inner cell layer and an outer cell layer, wherein the inner cell layer comprises inner cells which descend from said at least one pluripotent and/or totipotent cell and are capable of forming an embryo, and wherein the outer cell layer comprises outer cells which descend from said at least one trophoblast cell and are capable of forming at least a trophectoderm; and
  preferably culturing said at least double-layered cell aggregate to obtain a blastoid.

The invention further pertains to a double-layered cell aggregate and to a blastoid obtainable by this method, to a cell culture comprising a double-layered cell aggregate or blastoid, as well as to a method for growing an embryo, foetus or live animal from a blastoid by placing it in a uterus of a foster mother, or by growing the blastoid in vitro.

DESCRIPTION OF FIGURES

FIG. 1a: Microwell array chips and a 12-well plate.

FIG. 1b: freely suspended mouse TS-cells (green) seeded within microwells comprising an aggregate of mouse ES cells. Scale bar is 200 um.

FIG. 1c: An ES-TS cell cluster as a non-layered (c left) and double layered (c right) aggregate of trophoblast stem cells on the outside (green), and embryonic stem cells on the inside (red). Picture taken 24 hours after seeding the TS cells.

FIG. 1d: A blastoid comprising a trophectoderm (d left, green) and a distinct inner cell mass (d left, red), as well as, upon cavitation, a blastocoel (d right, inside cavity). Picture taken 70 hours after seeding the TS cells. Scale bar is 200 um.

FIG. 2a: Pluripotency of the trophectoderm in a blastoid as observed by nuclear CDX2 expression in trophoblast stem cells. aa: DNA staining using DAPI dye and antibody staining specific for CDX2. ab: Antibody staining specific for CDX2.

FIG. 2b: Pluripotency of the inner cell mass in a blastoid as observed by nuclear Oct4 expression in embryonic stem cells. ba: DNA staining using DAPI dye. bb: H2B-RFP molecular marker expressed into the nuclei of ES cells. bc: antibody staining against Oct4.

FIG. 2c: Formation of the epiblast as observed by Nanog expression and the primitive endoderm as observed by Sox17 and PDGFRa expression. Ca: Sox17 (green) and Nanog (red) fluorescent reporters expressed in ES cells. Cb: Sox17 (green) and Nanog (red) fluorescent reporters expressed in ES cells in combination with a bright field picture. Cc: F-actin staining using Phalloidin (red) and PDGFRa (green) fluorescent reporter in ES cells.

FIG. 3a: in vitro development of a blastoid to a gastrula stage by an extension of the Epiblast (Ep.), the formation of a Visceral Endoderm (V.E.) and the formation of an Ectoplacental cone (Ect. C.)

FIG. 3b-c: the in vivo development of a blastoid inside a uterus (b) results in the formation of a decidua (c) which includes a further developed embryo.

FIG. 4a: effect of the concentration of Y27632 on efficiency of engulfment during the formation of ES-TS cell clusters after 24 hours of culture.

FIG. 4b: effect of TS cell number on efficiency of engulfment during the formation of ES-TS clusters after 24 hours of culture.

FIG. 4c: yield of cavitated blastoids as a function of average ES cell number per microwell, The yield of cavitated blastoids is described by the percentage of ES-TS cell clusters that were cavitated after 96 hours of culture, thus forming an artificial blastocyst or blastoid. Cavitation was enhanced using 10 uM CHIR99021.

FIG. 4d: size of inner cell mass (ICM) as a function of the average number of ES-cells seeded per microwell. Size of ICM, measured as the projection area of the ES cell cluster inside the cavitated blastoid, increases with increasing numbers of ES cells seeded per microwell.

FIG. 4e: Increasing concentrations of Wnt pathway activator CHIR99021 positively correlate with an increase in the yield of cavitated blastoids.

FIG. 4f: PKA activation by addition of 8Br-cAMP up to a concentration of 1000 μM positively correlates with an increase in the size of ICM.

FIG. 4g: Akt activation with IGF2 and MAPK activation with HB-EGF positively correlates with an increase of Cdx2 expression as shown via CDX2 immunostaining.

FIG. 4h: Wnt pathway activation using the GSK3 inhibitor CHIR99021 (3 uM) or the Wnt ligand Wnt3a increases the yield of cavitated blastoids. The inhibition of Wnt signalling using the Wnt inhibitor XAV939 prevents the cavitation of blastoids.

FIG. 4i: influence of Wnt, PKC and PKA pathways on cavitation of ES-TS cell clusters. The control group included only CHIR99021 3 uM as a cavitating agent. The addition of cAMP, Indo.V and cAMP+Indo. V to CHIR99021 increase the yield of blastoids cavitation.

DETAILED DESCRIPTION

Figure 1:
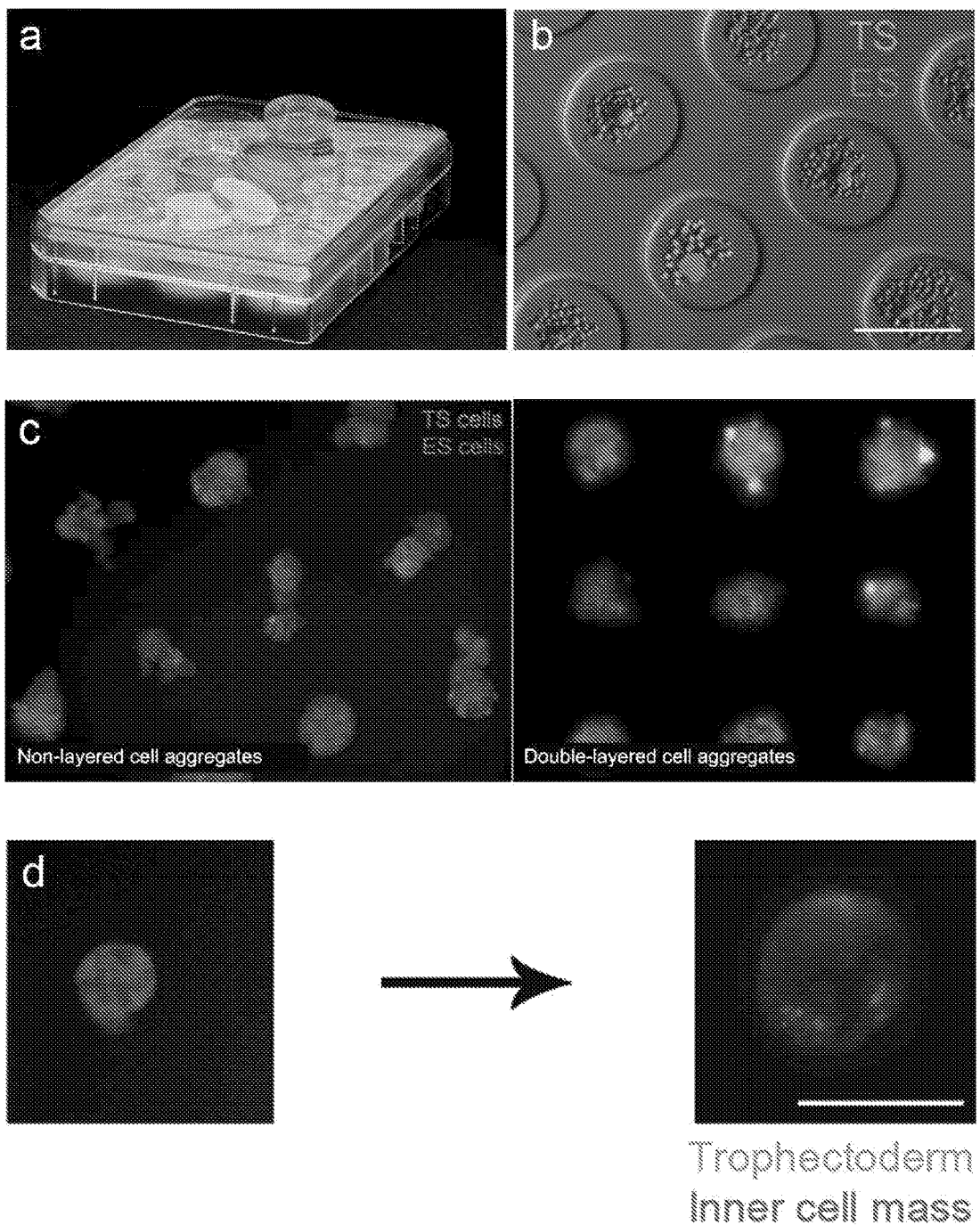
FIG. 1: In vitro preparation and development of a blastoid. (all scale bars are 200 μm.)

Mammals procreate naturally by fusing male and female germ cell lines (i.e. haploid cells, sperm and oocyte, respectively), from which combination a first cell (zygote) is formed. Any cellular structure resulting from continued growth of a zygote until formation of the foetus is called an embryonic structure, or an embryonic cell structure. Thus, the term "embryonic structure" reflects any structure occurring in the development from fertilisation to foetus, including among others the developmental stages of morula, blastocyst and gastrula. Thus, the term embryonic structure includes structures which are not yet cavitated into a blastocyst.

Cell division of the zygote under natural circumstances results in the morula, which is a spherical embryonic cell structure comprising 8 to 20 cells. The cells of the morula are totipotent, which means these cells are capable of differentiating into any embryonic or extra-embryonic cell types. When the morula matures, an internal, fluid-filled cavity is formed. This event correlates with the differentiation of the morula cells into an outer layer (trophectoderm) and the Inner Cell Mass (ICM or embryoblast). This cavitated cell structure is termed a blastocyst. Thus, a blastocyst is a stage in the development of a mammalian embryonic structure.

The trophoblast cells of the blastocyst surround the inner cell mass (ICM) as well as the fluid-filled blastocyst cavity (blastocoel). The trophoblast cells of the blastocyst develop further to form, among others, the ectoplacental cone, from which ultimately among others the placenta will form by combination with the inside wall of the uterus. The placenta is an organ that connects a developing foetus to the uterus' wall to allow nutrient uptake, waste elimination, and gas exchange via the mother's blood supply.

The inner cell mass consists of cells that have the capability to differentiate into any bodily tissue, and are therefore pluripotent. Also, inner cell mass cells form certain extra-embryonic tissues such as the yolk sac.

A blastocyst naturally develops further by proliferation and differentiation of the cells of the trophectoderm and of the ICM into cells other than embryonic stem cells. A first step of development of cells from the ICM results in the formation of an epiblast, a tissue that ultimately forms the animal, and a primitive endoderm, a tissue that ultimately forms, among others, the yolk sac.

In the epiblast, cells continue to differentiate by forming three tissue layers, the embryonic germ layers. Collectively these will form all the different tissue types present in the adult animal. The three embryonic germ layers are the endoderm, the ectoderm and the mesoderm; the endoderm will develop into among others the gastrointestinal tract and respiratory tract, the ectoderm will develop into among others the nervous system, hairs and nails, and the mesoderm will develop into among others muscle and connective tissue. Upon formation of the three embryonic germ layers, the embryonic structure has become a gastrula. Because a cell in any of the embryonic germ layers cannot naturally differentiate to form tissue descending from one of the other embryonic germ layers, a cell in an embryonic germ layer is multipotent, not toti- or pluripotent.

The gastrula develops, by further differentiation, proliferation and organization of the embryonic germ layers, into a foetus, going through various stages known in the art. For the scope of the present invention, an "embryo" is defined as any of a series of developmental structures starting as a blastocyst, and including all subsequent developmental stages, including e.g. the gastrula, until formation of the foetus. Thus, this term only refers to those structures occurring in the (natural) development from the blastocyst stage, and includes later structures up to the stage of the foetus. An embryo becomes a foetus when all organs have rudimentary formed.

A foetus is a mammal in the developmental stage after the embryonic stage and before birth, with fully differentiated but not yet fully grown organs.

Accordingly, a foetus is not encompassed by the term "embryo" or "embryonic structure".

In accordance with the invention, an initial cell aggregate is a cell aggregate comprising at least two cells, one of which is a trophoblast cell and the other of which is a pluripotent or totipotent cell. Preferably, the initial cell aggregate consists of two cell types, one of which is a trophoblast cell and the other of which is a pluripotent and/or totipotent cell. More preferably, the initial cell aggregate comprises a trophoblast cell and a pluripotent cell. Most preferably, the initial cell aggregate comprises a trophoblast cell and an embryonic stem cell (ES-cell), most preferably a trophoblast stem cell (TS-cell) and an embryonic stem cell (ES-cell).

In a preferred embodiment, an initial cell aggregate for use in the present method is formed from at least one trophoblast stem cell and at least one pluripotent stem cell, wherein the at least one trophoblast stem cell is capable of forming a trophectoderm and wherein the at least one pluripotent stem cell is capable of forming an inner cell mass.

In another embodiment, one of the cell types can have in addition to its own differentiation capability, a differentiation capability that is also present in the other cell type, such as for instance in a combination of a totipotent cell type with a trophoblast stem cell.

In another embodiment, the cell type that has the capability to differentiate into a trophectoderm does not have the capability to differentiate into an inner cell mass, and the cell type that has the capability to differentiate into an inner cell mass does not have the capability to differentiate into a trophectoderm.

In the context of the invention, an at least double layered cell aggregate is a layered cell aggregate comprising at least two radially positioned layers. Preferably, it is a spherical cell aggregate comprising an inner cell layer and an outer cell layer, wherein the inner cell layer comprises inner cells which descend from said at least one pluripotent and/or totipotent cell and are capable of forming an embryo, and wherein the outer cell layer comprises outer cells which descend from said at least one trophoblast cell and are capable of forming at least a trophectoderm.

One or more further layers, such as a third layer, of cells of a different cell type may be present, but preferably the at least double layered cell aggregate consists of two radially positioned cell layers consisting of an an inner cell layer and an outer cell layer, wherein the inner cell layer comprises inner cells which descend from said at least one pluripotent and/or totipotent cell and are capable of forming an embryo, and wherein the outer cell layer comprises outer cells which descend from said at least one trophoblast cell and are capable of forming at least a trophectoderm. This is called a double-layered cell aggregate.

However, for double- and higher layered cell aggregates it generally holds that the cells that ultimately form the blastoid or foetus are present in a single cluster located on the inside of the aggregate, while trophoblast cells are present on the outside. Preferably however, an (at least) double layered cell aggregate is a double layered cell aggregate.

Cavitation of the (at least) double layered cell aggregate results in formation of an artificial blastocyst, termed blastoid, and further culturing results in subsequent blastoid stages. It is particularly preferred if the one or more cells capable of forming the inner cell mass are essentially surrounded by cells with the capability of forming a trophectoderm. It is also particularly preferred if the surrounding cells capable of forming the trophectoderm are present in a single layer.

An artificial blastocyst is an embryonic cell structure with a trophectoderm-like tissue that surrounds a blastocoel and an inner cell mass-like tissue. An artificial blastocyst forms by cavitation of an at least double layered cell aggregate. The inner cell mass-like tissue may comprise a primitive endoderm.

A blastoid is the first stage in the development of an artificial blastocyst to foetus, but the term blastoid also covers further developmental stages of the artificial blastoid, up until formation of a fetus which descends from an artificial blastoid. A blastoid thus can also be called an artificial embryo, and includes all developmental stages of an artificial blastocyst obtained by the present method, and encompassing among others an artificial epiblast and an artificial gastrula. Upon formation of the foetus, the term blastoid no longer applies.

The trophectoderm-like tissue in the artificial blastocyst obtained by the present method is a tissue that behaves essentially as a naturally-formed trophectoderm. A trophectoderm-like tissue preferably is an in vitro generated trophectoderm with the same capability as a natural trophectoderm to develop into, at least, the ectoplacental cone and the placenta. A trophectoderm-like tissue can be, at least partially, pluripotent.

The inner cell mass-like tissue in the artificial blastocyst obtained by the present method is a tissue that behaves essentially as a naturally-formed inner cell mass. An inner cell mass-like (ICM-like) tissue preferably is an in vitro generated inner cell mass with the same capability as a natural inner cell mass to develop into, at least, any bodily tissue and certain extraembryonic tissues such as the primitive endoderm and the yolk sac. An ICM-like tissue can be, at least partially, totipotent.

Thus the invention also relates to a method for obtaining an at least double layered cell aggregate in vitro by
  forming an initial cell aggregate by combining at least one trophoblast cell and at least one pluripotent and/or totipotent cell and;
  inducing the organization of said cell aggregate to an at least double layered cell aggregate; and
  preferably, culturing the at least double layered cell aggregate to allow the formation of a cell structure wherein a trophectoderm-like tissue surrounds an inner cell mass and a blastocoel.

A mammalian animal is a placental animal, which develops naturally from a zygote in the presence of a placenta, inside a uterus until birth. For the scope of the present invention, a mammal includes all species that procreate through a blastocyst stage, including humans. However, inter alia because some countries do not allow the protection of inventions related to human embryos, it is preferred that a mammal refers to any mammalian animal, excluding humans. A preferred species of mammal is for instance a rodent, among which in particular a mouse or a rat, and further a horse, cow, pig, sheep, goat, dog, cat, monkey or human. Another preferred species of mammal is for instance a rodent, among which in particular a mouse or a rat, and further a horse, cow, pig, sheep, goat, dog or cat. An even more preferred animal is a mouse or a rat, and the most preferred animal is a mouse. In a preferred embodiment using different cell lines for forming the cell aggregate, the cells are derived from the same species.

Cell types for use in the present invention, such as trophoblast cells, pluripotent or totipotent cells, can be isolated from natural embryonic structures of any mammalian animal as described above. It is preferred, however, that at least one of the cell types for use in the present invention is obtained from a cell line, such as a cell line of trophoblast cells, a cell line of pluripotent cells, or a cell line of totipotent cells. More preferably, all cell types used in the present invention descend from cell lines. Cell lines may be obtained by any means known in the art.

The advantage of using cell lines for forming an at least double layered cell aggregate or a blastoid from cell lines is that cell lines can be stored and multiplied indefinitely, and that therefore harvesting cells from live animals can be avoided, A further advantage of using cell lines is that cell lines can easily be modified, such as by genetic modification, to obtain cells of the same cell type but with a specific genetic modification to alter its properties. Preferred genetic modifications are modifications which result a different genetic profile in the animal which is formed from the cells undergoing the genetic modification. A further advantage of using cell lines is that high numbers of at least double layered cell aggregates or blastoids can be obtained.

Preferably, in a method according to the present invention, the cell aggregate is formed using at least one diploid cell type. It is highly preferred that only diploid cells are combined. This allows for genetic modifications, which are fully and predictably expressed in an animal descendent from the used cell types, which is not possible when using haploid cells.

However, it is also possible to combine at least one aneuploid cell types, preferably one tetraploid cell type and at least one diploid cell type, preferably at least one tetraploid trophoblast cell derived from a tetraploid blastocyst and at least one diploid multipotent and/or totipotent cell. It is also possible to combine at least one trophoblast cell with at least one haploid cell.

A trophoblast cell for use in a method according to the present invention can be a trophoblast stem cell, or a cell which behaves essentially similar to a trophoblast stem cell. Preferably, a trophoblast stem cell (TS-cell) is used. Highly preferred is a trophoblast cell, such as a trophoblast stem cell, which is obtained from a cell line. A trophoblast cell is among others characterized by the expression of Eomes, GATA3, Tead4 and Tfap2c genes. A trophoblast cell is further characterized by its capability to form a trophectoderm.

A trophoblast cell may also be an induced trophoblast cell, which is a trophoblast cell obtained from a further differentiated cell. Preferably, an induced trophoblast cell also expresses the Eomes, GATA3, Tead4 and Tfap2c genes. Further preferably, a trophoblast cell is not an induced pluripotent cell, such as a cell which has been genetically modified to express Cdx2, as has been described in EP 2 088 191. A trophoblast cell may also be a totipotent cell.

Preferably, the trophoblast cell is a trophoblast stem cell (TS-cell). TS cells are characterized as cells with the potential to form extra-embryonic tissues including the placenta, and are therefore different from ES-cells. A TS-cell can be obtained by harvesting a zygote, a 2 to 128 cells stage embryo, a morula, a blastocyst or a post-implantation embryo (for example an embryonic stage "5.5 to 6.5 days post coitum") and establishing a TS-cell line culture for example as described in *Science* Volume 282, Issue 5396, 11 Dec. 1998, Pages 2072-2075 *Promotion to trophoblast stem cell proliferation by FGF4* Tanaka, S.[a], Kunath, T.[b], Hadjantonakis, A. K[a], Nagy, A.[b], Rossant, J or as described by Andras Nagy, Samuel Lunenfeld Research Institute; Marina Gertsenstein, Samuel Lunenfeld Research Institute; Kristina Vintersten, European Molecular Biology Laboratory; Richard Behringer, University of Texas M.D. Anderson Cancer Center, *Manipulating the Mouse Embryo: A Laboratory Manual (Third Edition)*, Cold spring harbour laboratory press, the contents of which are incorporated herein by reference.

Alternatively, TS-cells may be obtained by cellular reprogramming, so that the RNA or protein expression level is changed from a different cell type to a cell type which has a differentiation potential essentially similar to a TS-cell. TS cells obtained by cellular reprogramming are described by Chen Y, Wang K, Gong Y G, Khoo S K, Leach R. Roles of CDX2 and EOMES in human induced trophoblast progenitor cells. Biochem Biophys Res Commun. 2013 Feb. 8:431 (2)197-202. doi: 10.1016/j.bbrc.2012.12.135. Epub 2013 Jan. 8.

Preferably, trophoblast cells are not obtained from cellular reprogramming of ES-cells. An advantage of using at least one trophoblast cell over using other types of pluripotent cells as the trophoblast cell, such as ES-cells with a genetic modification that allows these ES-cells to form a trophectoderm-like structure by expression of Cdx2, is that trophoblast cells, be they harvested, descendent from a cell line or obtained through reprogramming, do not lead to the inadvertent participation of the trophoblast cells in the formation of the embryo, thus contaminating the genetic background of the organism obtained therefrom.

The at least one pluripotent and/or totipotent cell for use in the present invention are cell which have the capability to form an inner cell mass-like tissue. A pluripotent and/or totipotent cell can be a cell isolated from a natural embryonic structure, but preferably is obtained from a cell line. Also, an induced pluripotent and/or totipotent cell can be used, as long as it has the capability to form an inner cell mass-like tissue.

A pluripotent stem cell may be obtained by harvesting from a live animal or from an embryo. For further details of how a pluripotent stem cell can be obtained, references is made to *Proceedings of the National Academy of Sciences of the United States of America* Volume 78, Issue 12 II, 1981, Pages 7634-7638 *Isolation of a pluripotent cell line from early mouse embryos cultured in medium conditioned by teratocarcinoma stem cells*. Martin, G. R., the contents of which are incorporated herein by reference.

In addition, a pluripotent stem cell may be obtained by cellular reprogramming by changing the RNA and/or protein expression level from a further differentiated cell type to a cell type which is pluripotent, or has differentiation potential essentially similar to a pluripotent cell. In this regard, reference is made to *Cell* Volume 126, Issue 4, 25 Aug. 2006, Pages 663-676 *Induction of Pluripotent Stem Cells from Mouse Embryonic and Adult Fibroblast Cultures by Defined Factors*, Takahashi, K, Yamanaka, S, the contents of which are incorpote herein by reference. A pluripotent stem cell which is obtained by cellular reprogramming is called an induced pluripotent stem cell (iPS cell), and iPS cells are highly suitable for forming a cell aggregate according to the present invention.

As a preferred example, a pluripotent stem cell type for forming a cell aggregate according to the invention can be an embryonic stem cell (ES-cell). An ES-cell can be obtained by harvesting from a live animal or embryo. Preferably however, ES-cells are obtained from an ES-cell line culture derived from a harvested morula or a blastocyst. Alternatively, ES-cell-like-cells, which are cells with a similar capability as ES-cells, may be obtained by cellular reprogramming, so that the RNA, enzyme or protein expression levels are reversed from a further differentiated cell type to a cell type which has differentiation potential essentially similar to an ES-cell.

The obtention of rat embryonic stem cells is described by. Buehr, M, Meek, S, Blair; K, Yang, J, Ure, J, Silva, J, McLay, R., Hall J, Ying, Q.-L., Smith A, *Cell* Volume 135, Issue 7, 26 Dec. 2008, Pages 1287-1298. *Capture of Authentic Embryonic Stem Cells from Rat Blastocysts*, the contents of which are incorporated herein by reference.

The obtention of rhesus monkey embryonic stem cells this is described in: *Proceedings of the National Academy of Sciences of the United States of America*. Volume 92, Issue 17, 15 Aug. 1995, Pages 7844-7848. *Isolation of a primate embryonic stem cell line*. Thomson, J A., Kalishman, J, Galas, T G., Durning, M, Harris, C P, Becker R. A., Hearn, J P, the contents of which are incorporated herein by reference.

Alternatively or additionally, a pluripotent stem cell that can be used for forming a cell aggregate according to the invention can be a totipotent cell. A totipotent cell, in general, is a cell that has the capability to differentiate into any embryonic and into extraembryonic tissues, essentially comparable to a totipotent stem cell. A totipotent cell is thus a pluripotent stem cell. In the context of the present invention, a totipotent cell therefore can be used as a pluripotent stem cell. Thus, in one embodiment the cell aggregate comprises at least one totipotent cell. A totipotent cell may be isolated from an embryo or a mammal, preferably non-human, such as for instance a totipotent stem cell, or it can be obtained from a culture of totipotent cells as described by Macfarlan T S, Gifford W D, Driscoll S, Lettieri K, Rowe H M, Bonanomi D, Firth A, Singer O, Trono D, PfaffSL, *Embryonic stem cell potency fluctuates with endogenous retrovirus activity Nature* 2012 Jul. 5; 487 (7405): 57-63; doi: 10.1038/nature11244) or by Morgani S M[1], Canham M A, Nichols J, Sharov A A, Migueles R P, Ko M S, Brickman J M. *Totipotent embryonic stem cells arise in ground-state culture conditions*. *Cell Rep.* 2013 Jun. 27; 3(6):1945-57. doi: 10.1016/j.celrep.2013.04.034. Epub 2013 Jun. 6 or by Obokata H, Sasai Y, Niwa H, Kadota M, Andrabi M, Takata N, Tokoro M, Terashita Y, Yonemura S, Vacanti C A, Wakayama T. *Bidirectional developmental potential in reprogrammed cells with acquired pluripotency. Nature.* 2014 Jan. 30; 505(7485):676-80. doi: 10.1038/nature12969.

Preferably, at least one pluripotent cell is used in the method of the present invention. An advantage of using a pluripotent cell type over a totipotent cell type is that cell differentiation can be easier controlled. More preferably, the at least one pluripotent cell is an embryonic stem cell (ES-cell), even more preferably an embryonic stem cell obtained from a cell line.

In a much preferred embodiment, the initial cell aggregate is formed by combining at least one trophoblast cell, such as a trophoblast stem cell (TS-cell), with at least one embryonic stem cell (ES-cell).

Further preferably, the initial cell aggregate is formed by combining cells of the same species.

The at least one cell of either a trophoblast cell or a multipotent and/or totipotent cell that is used in the present method may be isolated directly, for instance from an isolated embryo, or obtained via reprogramming but preferably, the at least one cell is obtained from a cell line derived from a natural morula a natural blastocyst, a morula issued from nuclear transfer, a blastocyst issued from nuclear transfer, a morula issued from a tetraploid zygote or a blastocyst issued from a tetraploid zygote, a morula issued from in vitro fertilization, a blastocyst issued from in vitro fertilization. Preferably, a natural zygote is not used in the present method. In an even more preferred embodiment, the cell aggregate is not formed from a zygote. Further preferably, TS-cells used in the present method have not been obtained from genetic modification of ES cells.

This means that the present method is different from customary in vitro fertilization; in vitro fertilization makes use of two primary gametes, which are isolated from animal and merged, in vitro. In vitro fertilization thus makes use of the fusion of germ cells whereas, in the present method, only cell lines are used and no primary natural vehicle harvested from a pregnant mother such as gametes are used. Also, an at least double layered aggregate as formed in the present invention is not formed during in vitro fertilization, because generally the cell aggregate which cavitates in in vitro fertilization is a cell aggregate comprising only a single (totipotent) cell type, which cannot form a double layered aggregate. In in vitro fertilization, primary cell differentiation coincides with the formation of a blastocyst, so that an at least double layered cell aggregate is not formed. Also, in vitro fertilization does not involve in vitro cavitation of a cell aggregate, to form a blastocyst in vitro. The present method is an improvement over in vitro fertilization, because cell lines can be used, which is not possible for in vitro fertilization.

This means also that the present method is different from the method of obtaining a blastocyst with the tetraploid complementation technique: tetraploid complementation makes use of primary tetraploid blastocysts obtained from a 2 cell-stage embryo harvested from a pregnant mother whose cells are fused in vitro. In the present method, only cell lines are used and no primary natural vehicle harvested from a pregnant mother such as tetraploid blastocysts are used. In addition, the present method preferably comprises the combination of only haploid cells.

This also means that in a method according to the invention, chimera formation can be avoided. In chimera formation, the genetically altered cells that are injected into a harvested naturally grown morula or blastocyst, with a different genetic profile. Thus, the developing embryo is issued from the combination of the natural ICM and the injected cells and is not genetically homogeneous. In the present method a blastoid can result from the assembly of genetically homogeneous or heterogeneous cells.

Importantly, in a method for obtaining a blastoid according to the present invention, there is no requirement to directly use primary embryos or embryonic tissues from pregnant animals. The method is primarily based on cell lines, which can be multiplied in vitro. These cell lines can be derived from primary embryos or embryonic tissues, obtained via nuclear reprogramming or any other method to generate cell lines with potential to form a placenta, an inner cell mass or both. Optionally, a cell line for use in the present invention can be genetically altered such that the resulting blastoid or foetus displays characteristics that would not naturally have appeared.

The method thus provides a method to obtain a double layered cell aggregate and/or an artificial blastocyst and/or further developed blastoids without the requirement to sacrifice animals. It further allows for the formation of large numbers of genetically equal embryos or live animals, or of species with a controlled genetic modification, without the need to make and breed chimeras. This also lowers the amount of space, feed, work and legal requirements associated with embryonic research.

The method of the present invention comprises as a first step forming an initial cell aggregate by combining at least one trophoblast cell and at least one pluripotent and/or totipotent cell. Culturing this initial cell aggregate to obtain an at least double layered cell aggregate is achieved by seeding a precise number of each cell type, preferably in the presence of a Rho/Rock inhibitor.

An (at least) double-layered aggregate does not usually form spontaneously. For example, when ES-cells and TS-cells are co-cultured, they tend to spontaneously form a non-random cell cluster with TS-cells on the inside and ES-cells on the outside. Such an aggregate tends to evolve by forming attached but separated, non-engulfing aggregates of TS and ES cells (see FIG. 1c, left).

In contrast, in the method of the present invention, an (at least) double layered cell aggregate forms from at least one trophoblast cell and at least one pluripotent and/or totipotent cell, wherein the at least one pluripotent and/or totipotent cell are located on the inside of the at least double layered cell aggregate, whereas trophoblast cells are located on the outside. Thus, the at least one pluripotent and/or totipotent cell is engulfed by trophoblast cells, which is achieved by seeding a precise number of each cell type, preferably in the presence of a Rho/Rock inhibitor. One advantage of the engulfment of pluripotent and/or totipotent cells by trophoblast cells is that trophoblast cells limit the growth of the pluripotent and/or totipotent cells. The space created by the outer layer of trophoblast cells limits the growth of the pluripotent and/or totipotent cells.

In case of the use of ES-cells and TS-cells, ES cells are located on the inside of the double layered cell aggregate, while TS-cells are located on the outside. In this case, ES cells are engulfed by TS cells (see FIG. 1c, right), which is achieved by seeding a precise number of each cell type, preferably in the presence of a Rho/Rock inhibitor. One advantage of the engulfment of ES cells by TS cells is that TS cells limit the growth of the ES cells. The space created by the outer layer of TS cells limits the growth of the ES cells.

The number of cells required to obtain one initial cell aggregate comprising at least one trophoblast cell and at least one pluripotent and/or totipotent cell varies with the cell types used. The number of cells used is an important contributor to the efficiency with which an at least double layered cell aggregate forms. In general, one cell aggregate comprising at least one trophoblast cell and at least one pluripotent and/or totipotent cell comprises about 1-500, preferably about 10-50 pluripotent and/or totipotent cells in addition to at least one, preferably 1-250, more preferably 8-200, and even more preferably 12-50 trophoblast cells.

In case a TS-cell, is combined with pluripotent cell, such as for example an ES-cell, 1-250, preferably 8-200, and more preferably 12-50 cells of the TS-cell are used to form the initial cell aggregate, and from 1-250, preferably 2-100 and more preferably 3-50 cells of the pluripotent cell are used to form the initial cell aggregate.

Specifically, in case ES-cells are combined with TS cells for forming the initial cell aggregate, the number of ES-cells per microwell is preferably 1 to 25, preferably 3 to 12 and more preferably 6 to 8 ES-cells. The number of used ES-cells is an important contributor to the efficiency of formation of an at least double layered aggregate, which in this case is an ES-TS cell cluster. The number of TS cells per microwell in this case is around 3 to 70, preferably 8 to 45 and more preferably 15 to 20 trophoblast cells.

This can for instance be achieved by seeding ES-cells in culture medium, such as ES medium, preferably homogeneously, at 1000-100000 cells/chip, preferably around 7000 cells/chip in 10 µl-10 ml, preferably 0.5-3 ml.

Seeding of the cell types can be done in any order suitable or practical for that cell type. Thus, all cell types may be added simultaneously or near simultaneously, preceded or followed by addition of culture medium. Also, a suitable cell culture medium may be added first, followed by the addition of at least one pluripotent and/or totipotent cell and at least one trophoblast cell, in any order. Also, pluripotent and/or totipotent cell(s) and/or trophoblast cell(s) may be added as a suspension in culture medium, or they may be suspended in another medium and followed by replacement of the medium by the culture medium. Pluripotent cells, such as ES-cells, and trophoblast cells, such as TS-cells, may first be combined and then supplemented with culture medium, or trophoblast cells may be added first, followed by the addition of culture medium and pluripotent cells in any sequential order.

It is generally preferred if the order of combining is such that a cell aggregate forms which has an outer layer with the capability of forming a trophectoderm and a core with the capability of forming an inner cell mass (an (at least) double layered cell aggregate).

It is further preferred if seeding is done sequentially. Sequential seeding allows for cells of the cell type seeded first to settle and aggregate, while continuously multiplying, prior to addition of the second cell type. Thus, an aggregate of the first seeded cell type forms, which upon addition of the second cell type may become surrounded by cells of the second seeded cell type.

It is therefore generally preferred, in sequential seeding, to first seed the at least one pluripotent and/or totipotent cell and allow these cells to settle. Settling cells may take from 1 minute to 3 days, preferably from 6 hours to 2 days, more preferably from 12 hours to 36 hours, and most preferably between 18 and 30 hours, such as approximately 24 hours.

After settling, the at least one trophoblast cell can be added, which during culturing also continuously multiplies, but at the same time aggregates to the first cell type to form an at least double layered cell aggregate. An at least double layered cell aggregate is highly preferred for formation of a blastoid according to the present invention.

This order of addition is particularly preferred in case ES-cells are used as the multipotent and/or totipotent cell, and TS-cells are used as the trophoblast cell, to form a double layered cell aggregate.

It is preferred if the initial cell aggregate is cultured in the presence of a Rho/Rock inhibitor, as is further described below. Culturing the initial cell aggregate in the presence of a Rho/Rock inhibitor facilitates the aggregation and/or the engulfment of the at least one trophoblast cell onto the aggregate of at least one pluripotent and/or totipotent cell, which results in formation of the at least double layered cell aggregate, which is evidenced by the increase in efficiency of engulfment (the surrounding of the inner cell type by the outer cell type) at higher concentration of Y27632, a Rho/Rock inhibitor, which can be seen in the Examples.

The (at least) double layered cell aggregate is subsequently cultured for a period of 1 to 100 days, preferably 0.25-6 days, more preferably about 3 days (or about 72 hrs), resulting in cavitation. Cavitation of the at least double layered cell aggregate forms an inner cell mass-like tissue, as well as a blastocoel, together surrounded by a trophectoderm-like tissue.

An (at least) double layered cell aggregate has a diameter of about 10 μm to 200 μm, and comprises about 2-100, preferably 4-50 and more preferably 5-40 cells.

In the preferred case in which the initial cell aggregate is formed by combining at least one TS-cell and at least one ES-cell, the double layered cell aggregate is called an ES-TS cell cluster. An ES-TS cell cluster can be distinguished from an embryoid body by the presence of an external layer of cells with the potential to form a trophectoderm and, subsequently, a placenta. This can be assessed by the expression of biological factor specific to the trophectoderm, for example transcription factors, for example the caudal type homeobox transcription factor CDX2.

ES- and TS cells can be of different genetic origin, such that one of the two types derives from a genetically different cell line than the other type. This genetic difference may be due to the cells originating from a different species, or it may be due to one or more genetic modifications to the ES- and/or TS cells. In case of genetic modification(s), it is preferred if the ES-cells carry the intended modification, however, both cell types may carry the same or different genetic modifications. Preferably however, the ES- and TS-cells derive from the same species.

Culturing of an ES-TS cell cluster can be done for a period of 1 to 100 days, preferably 0.25-6 days, more preferably about 3 days (or about 72 hrs), resulting in cavitation. Cavitation of the ES-TS cell cluster forms an inner cell mass essentially comprising ES-cells, as well as a blastocoel, together surrounded by a trophectoderm.

The at least double layered aggregate, which in a preferred embodiment comprising ES- and TS cells is called an ES-TS cell cluster, is highly preferred for forming an artificial blastocyst. In the (at least) double layered cell aggregate cavitation, epithelisation and maintenance of the pluripotency of the at least double layered cell aggregate results in an artificial blastocyst. Further culturing results in subsequent blastoid stages.

Cavitation, epithelisation and maintenance of pluripotency is achieved by modulation of at least one of the Wnt pathway, the PKA pathway and the PKC pathway, as further described below. Preferably, the Wnt pathway and one of the PKA and the PKC pathway are activated, and most preferably, all of the PKC, the PKA and the PKC pathway are activated as described below.

This forms a blastoid from an at least double layered cell structure, such as an ES-TS cell cluster, with high efficiency. In particular, the efficiency of blastoid formation from an (at least) double layered cell aggregate is higher than 10%, usually higher than 20%, and oftentimes higher than 30%. The high efficiency of blastoid formation is achieved by the efficient formation of double-layered aggregates with an external layer of cells expressing the transcription factors CDX2, Eomes and GATA3 and a core aggregate of cells expressing the transcription factors Oct4, Sox2 and at least partly Nanog.

The efficiency of blastoid formation is measured as the percentage of cavitated structures with (1) an external cellular layer expressing the transcription factors CDX2, Eomes and GATA3 and (2) an internal cellular aggregate expressing the transcription factors Oct4 and Sox2 and at least partly Nanog.

To maintain pluripotency of the resulting blastoid, it is further preferred to modulate at least one of the MAPK-pathway, the STAT-pathway, the Akt-pathway the Tgf-pathway and the Hippo pathway. Preferably, this is achieved by activation of at least one of the MAPK-pathway, the STAT-pathway, the Akt-pathway and the Tgf-pathway, and/or by inhibition of the Hippo pathway, as described below.

Preferably, at least two of the MAPK-pathway, the STAT-pathway, the Akt-pathway, the Tgf-pathway and the Hippo pathway are modulated. More preferably at least three of the MAPK pathway, the STAT-pathway, the Akt-pathway, the Tgf-pathway and/or the Hippo pathway are modulated, even more preferably at least four of the MAPK pathway, the STAT-pathway, the Akt-pathway, the Tgf-pathway and/or the Hippo pathway are modulated and most preferably all of the MAPK pathway, the STAT-pathway, the Akt-pathway, the Tgf-pathway and/or the Hippo pathway are modulated, as further described below.

Maintaining pluripotency of the blastoid facilitates further culturing of the blastoid into subsequent blastoid states up until formation of the fetus. Formation of the initial cell aggregate, of the at least double layered cell aggregate and of the final blastoid, can be achieved by combining at least one trophoblast cell and at least one pluripotent and/or totipotent cell by any means known in the art. Such combination can be achieved in a hanging drop setup, in cups of appropriate size such as beakers, erlenmeyers or eppendorf cups.

Preferably, forming a cell aggregate according to the present invention can be done by combining suitable cells of suitable cell types as described above in a suitable container. A suitable container preferably has a non-adherent surface. A non-adherent surface is a surface on which the cells are placed, and which has little or no adhesion tendency to the cells. Thus, the cells do essentially not adhere to this surface. Without wishing to be bound by theory, use of a non-adherent surface provides a driving force for the cells to not adhere to the surface, but instead adhere to each other, thus forming a cell aggregate for use in the present invention.

A non-adherent surface may be formed by coating a material with a non-adherent biological or artificial material, or a non-adherent surface may be obtained by suitably shaping a non-adherent material, or by other means known in the art. A container on or in which the cell aggregate can be formed will from hereon be called a scaffold.

Scaffolds with a non-adherent surface are made of or are coated with, for example, ethylene oxide, propylene oxide, polyethylene glycol, (PEG)-(co)polymers (for instance PLL-g-(PEG)), poly(ethylene oxide) (PEO) (co)polymers, agarose hydrogels, temperature-responsive materials below their Lower Critical Solution Temperatures (LCST) (for example Poly(N-isopropylacrylamide)), hydrophobic materials (for example olefin polymers), cell-repellent micro- and nanotopographies.

Thus, forming a cell aggregate according to the present invention is preferably achieved in a non-adherent scaffold. A non-adherent scaffold has at least one surface that does not essentially allow for the adherence of cells. Preferably, this is the side on or in which cells to form the aggregate are placed. A non-adherent scaffold can be formed from a non-adhering material, or can be formed from another material coated with a non-adherent material. A non-adherent petri dish or tube may for example be used as scaffold, but preferably, the scaffold has a plate-like shape, such as for instance a more or less hexagonal, pentagonal, square, rectangular, triangular, oval or round shape.

More preferably, the scaffold comprises at least one suitable cavity or channel. Preferably, multiple cavities or channels are present on a scaffold. It is preferred if these cavities or channels are somewhat larger than the size of the cell aggregate to be formed. Suitable cavities and channels are small, such as for instance 20-5000 µm in diameter, more preferably 100-1000 µm, and most preferred are cavities of 100-500 µm, especially approximately 200 µm in diameter. Suitable cavities or channels may be obtained by any means known in the art. The diameter is defined as the longest possible straight-line distance between any two opposite points on the circumference of the opening of the cavity or channel. The channel or cavity has a closed bottom, and at least the surface of the inside of the cavity or channel comprises a non-adherent material.

Preferably, a cavity has a shape in which the length and breadth are of approximately similar order of magnitude. The depth, also, is of approximately the same order of magnitude. Such a cavity is called a microwell. For the present invention, it is preferred if the non-adherent scaffold comprises microwells. A microwell is preferably a cavity the length of which is up to about 5 times, preferably 3 times and more preferably approximately equal to its breadth, and which depth is no more than 10 times, preferably no more than 5 times, and more preferably up to 3 times its breadth.

The length of a microwell is defined as the longest possible straight-line distance between any two opposite points on the circumference of the opening of the microwell. Thus, the length of the microwell is considered its diameter, which is preferably for instance 20-5000 µm, more preferably 100-1000 µm, and most preferably 100-500 µm, especially approximately 200 µm. The breadth of a microwell is defined as the longest straight-line distance between any two opposite points on the circumference of the opening of the microwell perpendicular to its length.

The various cross-sectional areas of a microwell, among which those perpendicular and parallel to the surface of the scaffold, may be of any shape, including irregular shapes, but preferably, possible cross-sectional areas of a microwell are independently square or approximately square, rectangular or approximately rectangular, triangular or approximately triangular, oval or approximately oval or round or approximately round. However, it is preferred if the microwell is cylindrical, and has an approximately round opening in the surface of the scaffold. Suitable microwells are for instance present on microwell plates, such as commonly used in the art.

Particularly preferred for use with the present invention are the microwells as may be present on agarose chips, which may for instance be inserted in 2, 4, 6, 8, 12, 18 or 24, 48, 96, 384 well plates (WP). A suitable method for the production and use of such agarose microwell plates has been previously described, which description is described by Rivron N C, Vrij E S, Rouwkema J, Le Gac S, van den Berg A, Truckenmüller RK, van Blitterswijk C A, Tissue deformation spatially modulates VEGF signaling and angiogenesis, Proc Natl. Acad Sci USA. 2012 May 1; 109(18)6886-91 and is incorporated herein by reference.

An agarose chip of 5-25 mm, in particular 11 mm, featuring 100-10000 microwells, more preferably approximately 1000 microwells, may preferably be used, for instance in conjunction with 12 well plates.

In case a non-adherent scaffold comprises microwells, it is advantageous to have multiple microwells arranged on a single scaffold. Preferably, these microwells are arranged in a regular pattern. This allows for high-throughput preparation of large numbers of blastoids.

For forming a cell aggregate according to the present method on a non-adherent scaffold, it is advantageous to have one or more cell types as described above present on the scaffold. If the scaffold comprises cavities, such as for instance microwells, it is preferred if the one or more cell types are present inside the microwell(s). Any microwell may contain cell types for use in the present method. Preferably, approximately the amount of cells required to form at least one cell aggregate are present in one microwell, and more preferably, the amount of cells present in a microwell is the amount required to obtain one cell aggregate comprising at least one trophoblast cell and at least one pluripotent and/or totipotent cell.

In the Rho/ROCK pathway, Rho is a small GTP-binding proteins member of the Ras family. Rho and one of its down-effectors ROCK play central roles in the organization of the actin cytoskeleton, the assembly of focal adhesions and actin stress fibers, the activation of FAK, the dynamic of microtubule, the transcription of genes and the progression of the cell cycle. Rho proteins cycle between an active GTP-bound state and an inactive GDP-bound state. The mammalian Rho GTPase family currently consists of three subfamilies, Rho (RhoA, RhoB and RhoC), Rac (Rac1, Rac2 and Rac3) and CDC42 (Cell Division Cycle-42) (CDC42Hs and G25K).

The activation state of Rho/ROCK is controlled by regulatory proteins such as GEFs (Guanine Exchange Factors). Target proteins of RhoA include the PAK (p21-Activated Kinase) family, Rho-kinase/ROK/ROCK (Rho-Associated Coiled-Coil-Containing Protein Kinase) or MBS (Myosin-Binding Subunit). The activation and inhibition state of the pathway can be assessed by measuring the relative F-actin content using for example flow cytometry, immunochemistry, polymerase chain reaction or western-blotting.

In the present invention, the Rho/ROCK pathway is preferably modulated, wherein modulation is preferably inhibition. Rho/ROCK inhibition as herein described can be achieved by any means known in the art. One preferred way of Rho/ROCK inhibition is achieved by addition of one or more of numerous compounds including but not restricted to Fasudil hydrochloride, GSK 269962, GSK 429286, H 1152 dihydrochloride, Glycyl-H 1152 dihydrochloride, HA 1100 hydrochloride, SB 772077B dihydrochloride, SR 3677 dihydrochloride, or Y-27632. These compounds can be used at concentrations between 1 and 1000 uM.

Preferably, Y27632, preferably its dihydrochloride, is used, for example at concentrations ranging from 1-400 uM, preferably at 20 uM. Inhibition of the Rho/ROCK pathway in the present invention has the advantage that this increases the formation of an at least double layered cell aggregate from the initial cell aggregate.

The Wnt pathway is a cell-signalling pathway regulating cell growth and differentiation. The activation of the Wnt pathway naturally occurs via the binding of a ligand including but not restricted to the Wnt proteins (e.g. Wnt3a) to a membrane receptor including but not restricted to Frizzled. The binding results in the activation of the pathway characterised, for example, by a displacement of GSK-3@ from APC/Axin, which results in a nuclear translocation of @-catenin and the subsequent recruitment of LEF/TCF DNA-binding factors as co-activators for transcription.

The activation of the Wnt pathway integrates signals from other pathways, including retinoic acid, FGF, TGF-β, and BMP, and modulates cellular growth and differentiation. In addition, the binding of Wnt ligands, can activate non-canonical pathways acting for example on the Rho, Rac, PKC or CamK2 signaling pathways.

The activation of the Wnt pathway is, for example, assessed by the phosphorylation of GSK3, and/or the phosphorylation and/or the nuclear translocation of beta-Catenin, and/or by the expression of transcriptional target genes as known in the art (e.g. TCF, AP-1, snail, fibronectin). Wnt activation can be assessed by Western blotting, immunocytochemistry or another method known in the art.

In the present invention, the Wnt pathway is preferably modulated. More preferably, modulation occurs by activation of the Wnt pathway by any means known in the art. The addition of the Wnt ligand Wnt3a or of the GSK3 inhibitor CHIR99021 is a preferred way of activating the Wnt pathway, preferably at 1-10 uM, more preferably at approximately 3 uM.

Alternatively, the Wnt-pathway can be activated by addition of lithium salts, for example LiCl, or chemical molecules known in the art, including but not restricted to 2-amino-4-[3,4-(methylenedioxy)benzyl-amino]-6-(3-methoxyphenyl)pyrimidine, 6-bromoindirubin-3'-oxime and/or deoxycholic acid 6-[[2-[[4-(2,4-dichlorophenyl)-5-(5-methyl-1H-imidazol-2-yl)-2pyrimidinyl]amino]ethyl]amino]-3-pyridinecarbonitrile.

Activation of the Wnt pathway in the present invention has the advantage that it increases the yield of cavitation of the at least double layered cell aggregate. An increasing concentration of a Wnt-pathway activator, such as for example CHIR99021, increases for example the cavitation success rate of an ES-TS cell cluster. At 20 uM, CHIR99021 leads to a near 30% blastoid yield, whereas at 3 uM, the blastoid yield is 10%.

The PKA pathway is controlled by G protein-coupled receptor and is used in cell communication. Upon activation of the PKA signaling pathway, the activated Gs alpha subunit binds to and activates the enzyme adenylyl cyclase which catalyzes the conversion of ATP into cyclic adenosine monophosphate (cAMP). The increases in concentration of cAMP lead to the activation of, for example the cyclic nucleotide-gated ion channels, the exchange proteins activated by cAMP (EPAC), the Protein Kinase A enzyme. PKA activation can be assessed for example by measuring CREB phosphorylation or other PKA specific proteins via western blot or immunofluorescence, as is known in the art.

In the present invention, the PKA pathway is preferably modulated. More preferably modulation occurs by activation of the PKA pathway by any means known in the art, such as by using PKA activators or by genetic modification. The activation of the PKA pathway using PKA activators, such as for example 8Br-cAMP, at a concentration of 0.1-10 mM, for example at the concentration of 1 mM, increases the yield of cavitation.

Protein kinase C also known as PKC is a family of protein kinase enzymes involved in controlling the epithelisation, cell-cell junctions and apical-basal polarization of cells. PKC enzymes are activated by signals such as increases in the concentration of diacylglycerol (DAG) or calcium ions ($Ca^{2+}$). Upon activation, protein kinase C enzymes are translocated to the plasma membrane by RACK proteins (membrane-bound receptor for activated protein kinase C proteins).

The activation of the PKC pathway can be assessed, via immunocytochemistry, by the membrane localization of PKC proteins or cell-cell junctions or apical-basal polarity proteins such as, for example, ZO-1.

In the present invention, the PKC pathway is preferably modulated. More preferably, this occurs by activation of the PKC pathway by any means known in the art. The activation of the PKC pathway using, for example, Indolactam V, for example at a concentration of 0.1-10 uM, for example 1 uM, increases the yield of cavitation.

The MAPK pathway is a cell-signaling pathway regulating growth and differentiation. The MAPK pathway is regulated by a wide variety of receptors including receptor tyrosine kinases (RTKs), integrins, and ion channels. The binding of a ligand including but not restricted to Fibroblast Growth Factor, Epithelial Growth Factor, Platelet-derived Growth Factor, Interferon Gamma, Tumor Necrosis Factor, Interleukins, Transforming growth factors, Heparin-Binding EGF-Like Growth Factor, Nerve growth factor, Brain-derived Neutrophic Factor and/or FAS ligand (also known as CD95L) modulates adaptors including Shc, GRB2 and Crk linking the receptor to a guanine nucleotide exchange factor, including SOS and C3G, and transducing the signal to small GTP-binding proteins (e.g. Ras, Rap 1). These small GTP binding proteins activate the core unit of the cascade composed of a MAPKKK (Raf), a MAPKK (MEK1/2), and MAPK (Erk). An activated Erk dimer can regulate targets in the cytosol and also translocate to the nucleus where it phosphorylates a variety of transcription factors regulating gene expression.

The activation of the MAPK pathway is assessed by the phosphorylation of MEK, ERK and/or P38 MAPK, and/or by the activation of transcriptional targets such as ER, ETS, Elk1, TIF1A and others as known in the art. This can be assessed by Polymerase Chain Reaction, Western blotting, immunocytochemistry or any other method known in the art.

In the present invention, the MAPK pathway is preferably modulated. More preferably, this occurs by activation of the MAPK pathway by any means known in the art. The MAPK pathway can be activated intracellularly via the activation/inhibition of members of the signaling cascade including but not limited to (i) RAS using small chemical molecules including ML099 (CID-888706), ML098 (CID-7345532), and ML097 (CID-2160985) and C6 Ceramide, (ii) RAF1 using small chemical molecules including Phorbol 12-myristate 13-acetate or Indolactam V, (iii) p38 using small chemical molecules including SB203580, (iv) phosphotyrosine phosphatase using small chemical molecules including 203695bpV(phen), Okaidic acid, 479775 α-Naphthyl Acid Phosphate.

Activation of the MAPK pathway is preferably achieved using the ligands Fibroblast Growth Factor 4 (FGF4) or Heparin-Binding EGF-like growth factor (HB-EGF), more preferably by adding 1.5-500 ng/ml of the protein FGF4 and HB-EGF to the medium, even more preferably by adding 15 ng/ml of FGF4 and 50 ng/ml of HB-EGF.

Activation of the MAPK pathway in the present invention has the advantage of maintaining the pluripotency of the trophectoderm as assessed by the expression of the transcription factor Cdx2.

The STAT pathway regulates the growth, survival and differentiation of cells. Cytokines including but not restricted to LIF, Il6 and Il11 bind and induce receptor dimerization, for example GP130, thus activating the associated Jaks proteins, which phosphorylate themselves and the receptor. The phosphorylated sites on the receptor and Jaks serve as docking sites for the SH2-containing Stats, such as Stat3, and for SH2-containing proteins and adaptors that link the receptor to MAP kinase, PI3K/Akt, and other cellular pathways. Phosphorylated Stat dimerizes and translocate into the nucleus to regulate target gene transcription.

The activation of the pathway can, for example, be assessed by the phosphorylation of STAT as observed for example by western blot.

In the present invention, the STAT pathway is preferably modulated. More preferably, this occurs by activation of the STAT pathway by any means known in the art. The pathway can be activated by a variety of ligands including Cytokines, Hormones and Growth factors, and their receptors stimulate the JAK/STAT pathway. Intracellular activation occurs when ligand binding induces the multimerization of receptor subunits. For some ligands, such as Epo (Erythropoietin) and GH (Growth Hormone), the receptor subunits are bound as homodimers while, for others, such as Ifns (Interferons) and ILs (Interleukins), the receptor subunits are heteromultimers. Il11 can be used for example at concentrations ranging from 1-100 ng/ml, preferably at 10 ng/ml. Il6 can be used for example at concentrations ranging from 30-3000 ng/ml, preferably at 300 ng/ml.

Activation of the STAT pathway in the present invention has the advantage of maintaining the pluripotency and the viability of the ICM as assessed by the size of the ICM and the expression of, for example, Oct4, Sox2 and Nanog and the pluripotency of the trophectoderm as assessed by the expression of Cdx2.

The Akt pathway, also known as the Protein Kinase B (PKB) pathway, is a cell-signaling pathway regulating transcription, translation, proliferation, protein synthesis, glucose/insulin metabolism, growth, and survival. The binding of a ligand including but not restricted to Insulin-like Growth Factor, Epithelial Growth Factor, Fibroblast Growth Factor, Heparin-Binding EGF-Like Growth Factor, Nerve growth factor, Brain-derived Neutrophic Factor, Platelet-derived Growth Factor, Vascular Endothelial Growth Factor and Insulin to the membrane-bound receptor tyrosine kinase (RTK) stimulates PI3K isoforms. PI3K catalyzes the production of phosphatidylinositol-3,4,5-triphosphate (PIP3) at the cell membrane. PIP3 in turn serves as a second messenger that helps to activate Akt.

Once active, Akt controls key cellular processes by phosphorylating substrates involved in apoptosis, protein synthesis, metabolism, and cell cycle. The activation of the Akt pathway is assessed by the phosphorylation of Akt. This can be assessed by Western blotting, immunocytochemistry or any other method known in the art.

In the present invention, the Akt pathway is preferably modulated. More preferably, this occurs by activation of the Akt pathway by any means known in the art. Integrins, B and T cell receptors, cytokine receptors, G-protein-coupled receptors (GPCR) and other stimuli are known to activate the Akt pathway.

The Akt pathway can be activated intracellularly by using small molecules. For example, the Akt pathway can directly be activated by modulating the 3-phosphoinositide dependent protein kinase-1 (also known as PDK1) or by inhibiting a Phosphatase and tensin homolog (PTEN) using small chemical molecules such as for example PS48 and VO-OHpic, respectively.

The Akt pathway can also be activated via the p38 MAPK pathway by osmotic shock, inflammatory cytokines, lipopolysaccharides (LPS) and Ultraviolet light. The activation of the Akt pathway is preferably done using the ligands insulin or Insulin-like growth factor 2 (IGF2), more preferably by adding 1-100 ng/ml of IGF2 to the medium, even more preferably by adding 10 ng/ml of IGF2.

The activation of the Akt pathway has the advantage of maintaining the pluripotency of the trophectoderm as assessed by the expression of Cdx2 and the viability of the ICM as assessed by the size of the ICM. The expression of the transcription factors CDX2, Eomes and GATA3 is assessed by Polymerase Chain Reaction or by immunocytochemistry. Using Polymerase Chain Reaction, the levels of expression of the transcription factor are preferably no more than 5 fold up-regulated or down regulated as compared to trophoblast stem cells cultured on top of a layer of Embryonic Fibroblast cells seeded on polystyrene plates, as known in the art.

The expression of the transcription factors CDX2, Eomes and GATA3 can also be assessed by immunohistochemistry. The maximum intensity of a fluorescent antibody specific for the transcription factor must be located within the nucleus and must be no more then 5 fold up-regulated or down regulated as compared to trophoblast stem cells cultured on a layer of Embryonic Fibroblasts cells seeded on polystyrene plates, as known in the art.

Activation of the Akt pathway helps in maintaining pluripotency of the blastoid during in vitro culturing.

The Tgf pathway is a cell-signalling pathway regulating cell growth, differentiation, and development. The binding of ligands including but not restricted to Transforming Growth Factor, Bone Morphogenetic Protein, Activin and/or Nodal induces the oligomerization of serine/threonine receptor kinases and phosphorylation of the cytoplasmic signaling molecules Smad2 and Smad3 for the TGF-β/activin pathway, or Smad1/5/8 for the bone morphogenetic protein (BMP) pathway. The phosphorylation of these smad2, 3, 1/5/8 induces the formation of protein complexes with the common signaling transducer Smad4 and their translocation to the nucleus.

Once activated, the Tgf pathway activates target genes including transcription factors AP-1, bZIP, RUNX, Fox and bHLH that lead to cellular growth, differentiation and development. The activation of the Tgf pathway is assessed by the phosphorylation of Smad2, 3, 4, 1, 5, 8 and by the activation of transcriptional targets such as AP-1, bZIP, RUNX, Fox, bHLH and others as known in the art. This can be assessed by Polymerase Chain Reaction, Western blotting, immunocytochemistry or any other method known in the art.

In the present invention, the Tgf pathway is preferably modulated. More preferably, this occurs by activation of the Tgf pathway by any means known in the art. Activation of the Tgf pathway in the present invention has the advantage of maintaining the pluripotency of the trophectoderm, which can be assessed by the expression of Cdx2 and/or by inducing the cavitation of the aggregate.

Activation of the Tgf pathway is preferably done using the ligand TGFb1, more preferably by adding 0.5-50 ng/ml of the ligand Tgfb1, even more preferably by adding 5 ng/ml of Tgfb1. Alternatively, the activation of the Tgfb1 pathway is done using the ligand activin, preferably by adding 0.1-100 ng/ml of activin A, even more preferably around 10 ng/ml.

The Hippo pathway is a cell-signalling pathway regulating cell growth, apoptosis and stem cell renewal. The Hippo pathway is involved in cell contact inhibition and regulated via Mst1/2 and LATS1/2, Merlin, KIBRA, RASSFs, and Ajuba; 14-3-3, α-catenin, AMOT, and ZO-2. The Hippo activity is asset via the shuttling of YAP/TAZ between the nucleus and the cytoplasm. Upstream signals regulating the Hippo signalling include cell-cell junction and polarization complexes, the cytoskeleton and GPCR ligands.

In the present invention, the Hippo pathway is preferably modulated. More preferably, this occurs by inhibition of the Hippo pathway by any means known in the art. It is preferred for the formation of an at least double layered cell aggregate and/or a blastoid that extracellular ligands are present, which modulate the Hippo signalling, more specifically GPCR ligands, even more specifically GPR30 ligands, for example Estradiol at 1-35 ng/ml, preferably 10 ng/ml, tamoxifen at 1-35 uM, preferably about 10 uM, or G-1 at 0.1-10 uM, preferably 1 uM (CAS 881639-98-1).

Modulation of the Hippo pathway as described herein has the advantage of inducing cavitation, epithelisation and maintenance of the pluripotency of the cell aggregate.

The present invention discloses methods for obtaining an at least double layered cell aggregate as described, wherein any combination of modulation (activation or inhibition) of one of the above pathways is applied.

The present invention also discloses methods for obtaining a blastoid as described, wherein any combination of modulation (activation or inhibition) of one of the above pathways is applied. Preferably, the preferred mode of modulation (activation or inhibition) described for each compound is applied as indicated.

The invention also discloses an in vitro cell culture comprising one or more of a Rho/ROCK inhibitor, a Wnt pathway modulator, a PKA pathway modulator, a PKC pathway modulator, a MAPK pathway modulator, a STAT pathway modulator, an Akt pathway modulator, a Tgf pathway modulator, a Hippo pathway modulator, and further comprising an (at least) double layered cell aggregate, or a cell culture of any combination of any one or more of these modulators with a double layered cell aggregate.

Also, the invention discloses an in vitro cell culture comprising one or more of a Rho/ROCK inhibitor, a Wnt pathway modulator, a PKA pathway modulator, a PKC pathway modulator, a MAPK pathway modulator, a STAT pathway modulator, an Akt pathway modulator, a Tgf pathway modulator, a Hippo pathway modulator, and further comprising a blastoid, or a cell culture of any combination of any one or more of these modulators with a blastoid.

An increase in blastoid yield is also achieved by an appropriate spatial confinement using a non-adherent scaffold, preferably comprising microwells, by the appropriate formation of a, at least, double layered aggregate and the appropriate modulation of the signalling pathways involved in cavitation and epithelisation processes and in the maintenance of pluripotency of the cell aggregate, by addition of specific compounds.

Inducing the organization is achieved by the methods defined above, i.e. by spatial confinement using a non-adherent scaffold, preferably comprising microwells, by inducing the formation of a, at least, double layered aggregate and/or by modulating the signalling pathways involved in cavitation and epithelisation processes and in the maintenance of pluripotency.

From the moment an embryonic cell structure derived from an artificial blastocyst has developed into a foetus, the term blastoid no longer applies. Instead, the foetus is referred to an "artificial foetus", which may have developed in vitro or in vivo. An in vivo developed artificial foetus is a foetus stemming from further development of a blastoid inside the uterus of a mammal. If such further development occurs in vitro, it is called an in vitro developed artificial foetus.

Preferably, a double layered cell aggregate or a blastoid is implanted in a foster mother. More preferably, a cell aggregate according to the invention is implanted after cavitation (i.e., as a blastoid), even more preferably 1-1000 hours after seeding the trophoblast cells, preferably 48-300 hours, such as approximately 110 hours. Further preferably, a blastoid is implanted after formation of a primitive endoderm, as can be assessed by any means known in the art.

A cell line for forming a cell aggregate of the present invention can be modified genetically and epigenetically using methods of genetic engineering known in the art or using biological or chemical factors such as proteins, enzymes or chemicals. Such a modified cell line may have the potential for contribution to the formation of embryonic or extra-embryonic tissues as described in for instance Macfarlan T S, Gifford W D, Driscoll S, Lettieri K, Rowe H M, Bonanomi D, Firth A, Singer O, Trono D, Pfaff S L, *Embryonic stem cell potency fluctuates with endogenous retrovirus activity Nature* 2012 Jul. 5; 487 (7405): 57-63; doi: 10.1038/nature11244;

Morgani S M, Canham M A, Nichols J, Sharov A A, Migueles R P, Ko M S, Brickman J M, *Totipotent embryonic stem cells arise in ground-state culture conditions. Cell Rep.* 2013 Jun. 27; 3(6):1945-57. doi: 10.1016/j.celrep.2013.04.034. Epub 2013 Jun. 6.)

Bidirectional developmental potential in reprogrammed cells with acquired pluripotency. Obokata H, Sasai Y, Niwa H, Kadota M, Andrabi M, Takata N, Tokoro M, Terashita Y, Yonemura S, Vacanti C A, Wakayama T. *Nature.* 2014 Jan. 30; 505(7485):676-80. doi: 10.1038/nature12969. the contents of which are incorporated herein by reference.

A cell line for use in forming the cell aggregate can be genetically modified prior or during the formation of a blastoid according to the present invention. Genetic modification can include the modification of an endogeneous sequence, the insertion of an additional sequence, the partial or total removal of a sequence, or any combination of these approaches.

Also, one or more of the cells for use in the present method may optionally be modified by a known method to result in a marked cell. Such markers can be a fluorescent protein, for example a fluorescent protein whose expression is regulated and reflects the expression of a gene of interest.

A cell line for forming a cell aggregate according to the present invention can be stored almost indefinitely as is known in the art. Storing cells means that cells are inserted in a container together with culture medium. The culture medium functions to keep cells alive, promote their division and prevent their differentiation. Thus the cell number in the culture grows, so that repetitive passaging of a portion of cells is required. This portion is then introduced in a container in combination with culture medium, while the non-selected remainder of cells is either discarded, cultured in a different container or frozen for preservation.

Retaining of cells is a general term encompassing among others storing and expanding, with the basic general meaning of keeping cells alive and proliferating, while remaining undifferentiated. This usually also requires a suitable culture medium. A suitable culture medium for the culturing of cells for forming the cell aggregate of the invention is any cell culturing medium appropriate for cells; a cell culture medium appropriate for cells is known in the art.

Generally, a cell culture medium appropriate for cells comprises for instance vitamins, amino acids, and inorganic salts. However, the exact composition of a cell culture medium may vary with cell type, and the skilled person knows how to obtain a cell culture medium appropriate for each cell type used in the present invention.

For example, a basic medium for pluripotent and/or totipotent cells, in particular ES cells, is for instance Dulbecco's Modified Eagle's Medium, which comprises Foetal Bovine Serum (FBS)(10% v/v), L-Glutamine (2 mM), beta-mercaptoethanol (50 mM), Penicilline/streptomycin (50 µg/ml), Non-essential amino acids (1% v/v) and Leukemia inhibitory factor (10 µg/L). As a second example, a basic medium for TS cells is RPMI 1640 which uses a bicarbonate buffering system and alterations in the amounts of amino acids and vitamins (77% v/v), FBS (20% v/v), Penicilline/streptomycin (50 µg/ml), Sodium Pyruvate (100 mM), L-Glutamine (2 mM), beta-mercaptoethanol 50 mM, FGF-4 (25 ng/ml), Heparin (1 µg/ml).

Another suitable medium for storage, expansion and retaining of pluripotent and/or totipotent cells, in particular ES cells, is a serum-free medium including the B27 and N2 components, which is known in the art and which can for instance be made by combining the below compounds in approximately the given quantities. DMEM/F12 medium (48% v/v), Neurobasal medium (48% v/v), L-Glutamine (2 mM), N2 supplement (1% v/v), B27 supplement (2% v/v), Sodium pyruvate (100 mM), Non Essential Amino Acids (1% v/v), beta-Mercaptoethanol (0.1 mM), Penicilline/streptomycin (50 µg/ml), BSA (5 mg/ml). Such a medium is described by Ying Q L, Wray J, Nichols J, Batlle-Morera L, Dobie B, Woodgett J, Cohen P, Smith A. The ground state of embryonic stem cell self-renewal. Nature. 2008 May 22:453 (7194)519-23. doi: 10.1038/nature06968.

Another suitable medium for storage, expansion and retaining of pluripotent and/or totipotent cells, in particular ES cells, is a serum-free medium known in the art as E8 medium and described by Chen G$^1$, Gulbranson D R, Hou Z, Bolin J M, Ruotti V, Probasco M D, Smuga-Otto K, Howden S E, Diol N R, Propson N E, Wagner R, Lee G O, Antosiewicz-Bourget J, Teng J M, Thomson J A. Nat. Methods. 2011, "Chemically defined conditions for human iPSC derivation and culture".

Mouse totipotent cells for use in forming a cell aggregate according to the present invention, such as totipotent stem cells obtained by harvesting and/or culturing as a cell line, and totipotent cells obtained by reprogramming of for instance pluripotent stem cells, or from further differentiated cell types, can, for example, be retained in the basic medium for ES cells as described above or as described in Macfarlan T S, Gifford W D, Driscoll S, Lettieri K, Rowe H M, Bonanomi D, Firth A, Singer O, Trono D, Pfaff S L, *Embryonic stem cell potency fluctuates with endogenous retrovirus activity Nature* 2012 Jul. 5; 487 (7405): 57-63; doi: 10.1038/nature11244) or Morgani S M$^1$, Canham M A, Nichols J, Sharov A A, Migueles R P, Ko M S, Brickman J M. *Totipotent embryonic stem cells arise in ground-state culture conditions. Cell Rep.* 2013 Jun. 27; 3(6):1945-57. doi: 10.1016/j.celrep.2013.04.034. Epub 2013 Jun. 6 or *Bidirectional developmental potential in reprogrammed cells with acquired pluripotency*. Obokata H, Sasai Y, Niwa H, Kadota M, Andrabi M, Takata I V, Tokoro M, Terashita Y, Yonemura S, Vacanti C A, Wakayama T. *Nature.* 2014 Jan. 30; 505(7485):676-80. doi: 10.1038/nature12969., the contents of which are incorporated herein by reference.

Preferred pluripotent cells suitable for forming an initial cell aggregate according to the present invention are embryonic stem cells (ES-cells). For instance, mouse ES-cells can be retained in one of the culture media described above. Specifically, ES-cells can be expanded by seeding the cells on a cell layer of embryonic fibroblast ("mEF") cells, as is known in the art. The layer of mEF-cells is obtained by seeding of the mEF cells in a tissue culture plate at a cell density of between 1000 and 50000 cells/cm$^2$, preferably at a density between 10000 and 25000 cells/cm$^2$ and subsequent expansion. Attachment of mEF cells can be done in one of the culture mediums described above. This may take a few hours to a few days, preferably about one day. This procedure results in an EF layer, upon which ES cells can be seeded. Mouse ES cells are seeded on the EF cell layer at a cell density of between 1 and 50000 cells/cm$^2$, preferably at a density between 10000 and 25000 cells/cm$^2$, in a suitable culture medium. Mouse ES cells seeded on mEF cells are preferably expanded in the presence of a signal transduction and transcription protein signalling activator (STAT protein signalling activator), such as for instance Leukemia inhibitory factor which can be used in a concentration from 1 to 1000 µg/L. Alternatively, ES-cells can be cultured without feeder layers for example on a coating of gelatin or on a coating of extra-cellular matrix or on microbeads as known in the art, for example using mEF conditioned medium, for example using chemical compounds PD0325901 1 µM, CHIR99021 3 µM as previously described in *Nature.* 2008 May 22; 453(7190'519-23. The ground state of embryonic stem cell self-renewal. Ying Q L, Wray J, Nichols J, Batlle-Morera L, Dobie B, Woodgett J, Cohen P, Smith A.

As a second example, mouse TS cells can be cultured as known in the art for example as described in *Manipulating the Mouse Embryo: A Laboratory Manual (Third Edition)*. Andras Nagy, Samuel Lunenfeld Research Institute; Marina Gertsenstein, Samuel Lunenfeld Research Institute; Kristina Vintersten, European Molecular Biology Laboratory; Richard Behringer, University of Texas M. D. Anderson Cancer Center Cold spring harbour laboratory press or in serum-free condition, for example in TX medium, for example as described by Kubaczka C, Senner C, Araúzo-Bravo M J, Sharma N Kuckenberg P, Becker A, Zimmer A, Brüstle O, Peitz M Hemberger M, Schorle H *Derivation and Maintenance of Murine Trophoblast Stem Cells under Defined Conditions. Stem Cell Reports.* 2014 Jan. 30; 2(2):232-42. doi: 10.1016/j.stemcr.2013.12.013.eCollection 2014 Feb. 11.

For example, TS cells are seeded on an EF-cell layer as described above at a density of between 1 and 50,000 cells/cm$^2$, preferably between 3,000 and 10,000 cells/cm$^2$ and cultured in a suitable medium (see below). Mouse TS cells are preferably maintained on EF cells, optionally in the presence of a protein activating the Mitogen-Activated Protein Kinases (MAPK) and/or the Extracellular-regulated Receptor Tyrosine kinase, for example Fibroblast Growth Factor 4 (25 ng/ml) and/or a protein part of the Transforming Growth Factor superfamily, for example activin (preferably around 10 ng/ml) and/or tgfb1 (preferably 1-10 ng/ml) or a functionally similar compound.

The dissociation of expanded ES- or TS cells from an mEF cell layer is conveniently performed by the known enzymatic or non-enzymatic methods, preferentially by trypsinization, in which trypsin enzyme is added to loosen the cell layers or aggregates. Subsequently, in case a feeder-layer was used, mEF cells are depleted by incubutation for between 5 and 60 minutes, preferably around 20 minutes, in a fresh plate, preferably made of plastic, such as polystyrene, which results in the mEF cells adhering to the fresh plate. Because the ES- or TS-cells do not adhere as fast as the mEF-cells, the ES- or TS-cells can be separated from the mEF-cells. This procedure may advantageously be repeated, and allows for separation of mEF-cells from ES or TS cells, resulting in pure ES- or TS-cells suspended in culture medium. The methods of enzymatic and non-enzymatic dissociation of cells including the method of trypsinization is well-known in the art, see for example *Manipulating the Mouse Embryo: A Laboratory Manual (Third Edition)*. Andras Nagy, Samuel Lunenfeld Research Institute; Marina Gertsenstein, Samuel Lunenfeld Research Institute; Kristina Vintersten, European Molecular Biology Laboratory; Richard Behringer, University of Texas M.D. Anderson Cancer Center, Cold spring harbour laboratory press, the contents of which are incorporated herein by reference.

Thus, TS-cells are trypsinized, depleted from EF and resuspended in TS cell culture medium. This suspension is seeded to the microwells containing the ES cell clusters in order to seed around 3 to 70, preferably 8 to 45 and more preferably 15 to 20 trophoblast stem cells per microwell. TS-cells settle in around fifteen minutes to an hour, after which they can be counted under a bright field microscope via conventional technique known in the art and described below. This can for instance be achieved by seeding TS-cells in culture medium, such as TS medium, preferably homogeneously, at 1000-100000 cells/chip, preferably around 17000 cells/chip in 10 μl-10 ml, preferably 0.5-3 ml.

Culturing cells with the aim of storing or retaining for use in the present method is preferably performed in an incubator, at a temperature optimal for the species, which in general is 10-60° C., preferably 25-45° C., more preferably 35-40° C.

Culturing cells for forming a cell aggregate of the present method, such as the initial cell aggregate, the (at least) double layered aggregate or an artificial blastocyst is preferably performed in an incubator, at a temperature optimal for the species, which in general is 10-60° C., preferably 25-45° C., more preferably 35-40° C.

An initial cell aggregate of the invention has the capability of differentiating into a trophectoderm-like tissue and into an inner cell mass-like tissue. The inner cell mass has the capability to differentiate into a primitive endoderm as shown for example by the expression of Sox17 and PDGFRa. Thus, an initial cell aggregate for use in the present invention can comprise a single cell type with the capability of differentiating into a trophectoderm and an inner cell mass. This is for instance the case in a cell aggregate comprising one or more totipotent cells, preferably in the case when the cell aggregate comprises essentially only totipotent cell types. This embodiment of the invention is encompassed by the invention, although it is less preferred.

In the preferred embodiment of ES-cells combined with TS-cells for forming the initial cell aggregate, a culturing period of hours to a few days for the ES cell culture, especially approximately one day, is preferred, before addition of the TS-cells, to allow for the formation of an initial ES cell cluster.

Preferably, in case at least one trophoblast stem cell and ES cells are used as the at least one pluripotent stem cell as defined above, the ES-cells are allowed to settle and aggregate before addition of the TS-cells. Settling of the ES-cells allows for the formation of an initial cell cluster, which after addition of the TS-cells and of a regulator of the cytoskeleton, for example a Rho/ROCK inhibitor, for example the p160ROCK inhibitor Y27632, for example at a concentration of 1-100 uM, preferably 2-50 uM, such as for example about 20 uM, can be surrounded by the TS-cells, thus forming a double layered aggregate which in this case is is called an ES-TS cell cluster.

A culture medium, such as B27N2, TX or E8 medium possibly supplemented with for instance a cytoskeletal tension inhibitor such as a Rho/ROCK inhibitor, or with a Wnt modulator, preferably a Wnt activator, a PKA modulator, preferably a PKA activator, a PKA modulator, preferably a PKC activator, a MAPK modulator, preferably a MAPK activator, a STAT modulator, preferably a STAT activator, an Akt modulator, preferably a Akt activator, a Tga modulator, preferably a Tga activator, and/or a Hippo modulator, preferably a Hippo inhibitor as described above, may be advantageously added before, after or during counting. E8 medium is known in the art and its composition has been described in Nat. Methods. 2011, "Chemically defined conditions for human iPSC derivation and culture" Chen G[1], Gulbranson D R, Hou Z, Bolin J M, Ruotti V, Probasco M D, Smuga-Otto K, Howden S E, Diol N R, Propson N E, Wagner R, Lee G O, Antosiewicz-Bourget J, Teng J M, Thomson J A.

Also in this case, it is preferred that seeding of the cells occurs homogeneously, as described elsewhere. Also the TS-cells are preferably allowed to settle after addition of the medium.

As a rough guidance, for formation of an initial (at least) double layered cell aggregate and a subsequent blastoid from ES- and TS-cells according to the present invention it is preferred that one microwell, which advantageously has a diameter of about 200 μm, preferably comprises about 9 ES cells as a single cell cluster, to which about 17 TS-cells and 20 uM of a Rho/ROCK inhibitor, for example Y27632 are added. This results in a ES-TS cell cluster, which can be cultured to form an artificial blastocyst and subsequently a blastoid according to the invention.

The average number of cells per cavity can be counted by methods known in the art. One appropriate method to seed an appropriate number of cells is the use of a hemocytometer to evaluate the cellular concentration of a single cell suspension and the subsequent seeding of an appropriate number of cells. Given that in a single cavity the success of forming a blastoid depends in part on the number and type of cells present, it is practical to seed cells as homogeneously as possible in the various cavities used.

In accordance with the invention, culturing of the (at least) double layered cell aggregate, preferably the ES-TS cell cluster, is carried out in such a way that it preferably results in cavitation of the (at least) double layered cell aggregate. Cavitation is the process of forming a globular structure from an (at least) double layered cell structure via the differentiation and proliferation of cells. The inside, fluid-filled cavity, termed the blastocoel, is surrounded by a layer of trophectoderm cells characterised by their potential to form a placenta. The trophectoderm is also characterised by cells expressing the transcription factors CDX2, Eomes and GATA3. The cavitation process also results in an inner cell mass and in a blastocoel, surrounded by a trophectoderm.

Cavitation can be achieved by choosing appropriate culturing conditions or it can be happen spontaneously. In the latter case, cavitated aggregates may be selected from all the cultured aggregates. Culturing in this case can be done in any suitable culture medium known in the art and/or described above.

In one embodiment, cavitation may be achieved by culturing the cell aggregate in any culture medium, and allowing cavitation to occur. This, however, occurs with low success rate, such as for instance 5 per 1000. Thus, for obtaining a blastoid by this method, properly cavitated cell aggregates have to be selected from a population of cultured cell aggregates. Selection can be done by visualising the formation of a blastocoel under a conventional microscope.

However, a blastoid can preferably be obtained according to the invention by culturing the cell aggregate in a culture medium with cavitation-inducing components as described above. The cavitation-inducing components can be supplied as solids or in solution to a cell culture, but preferably, they are added to a known culture medium, such as B27N2, E8 or TX, to obtain an elaborated culture medium used for culturing the cells forming the cell aggregate, and/or for culturing the cell aggregate to obtain the artificial blastocyst.

In one preferred embodiment cavitation of the cell aggregate is achieved by modulation of at least one of the Wnt-pathway, the PKC pathway and/or the PKA pathway, and preferably also of the the MAPK pathway, the STAT pathway, the Akt pathway, the Tgf pathway and/or the Hippo pathway as described below.

In a most preferred embodiment, cavitation of the cell aggregate is achieved by modulation of the Wnt pathway, the PKC pathway and the PKA pathway. The influence of the Wnt, the PKC and the PKA pathways on cavitation of the cell aggregate are described in FIG. 4.

Figure 4:
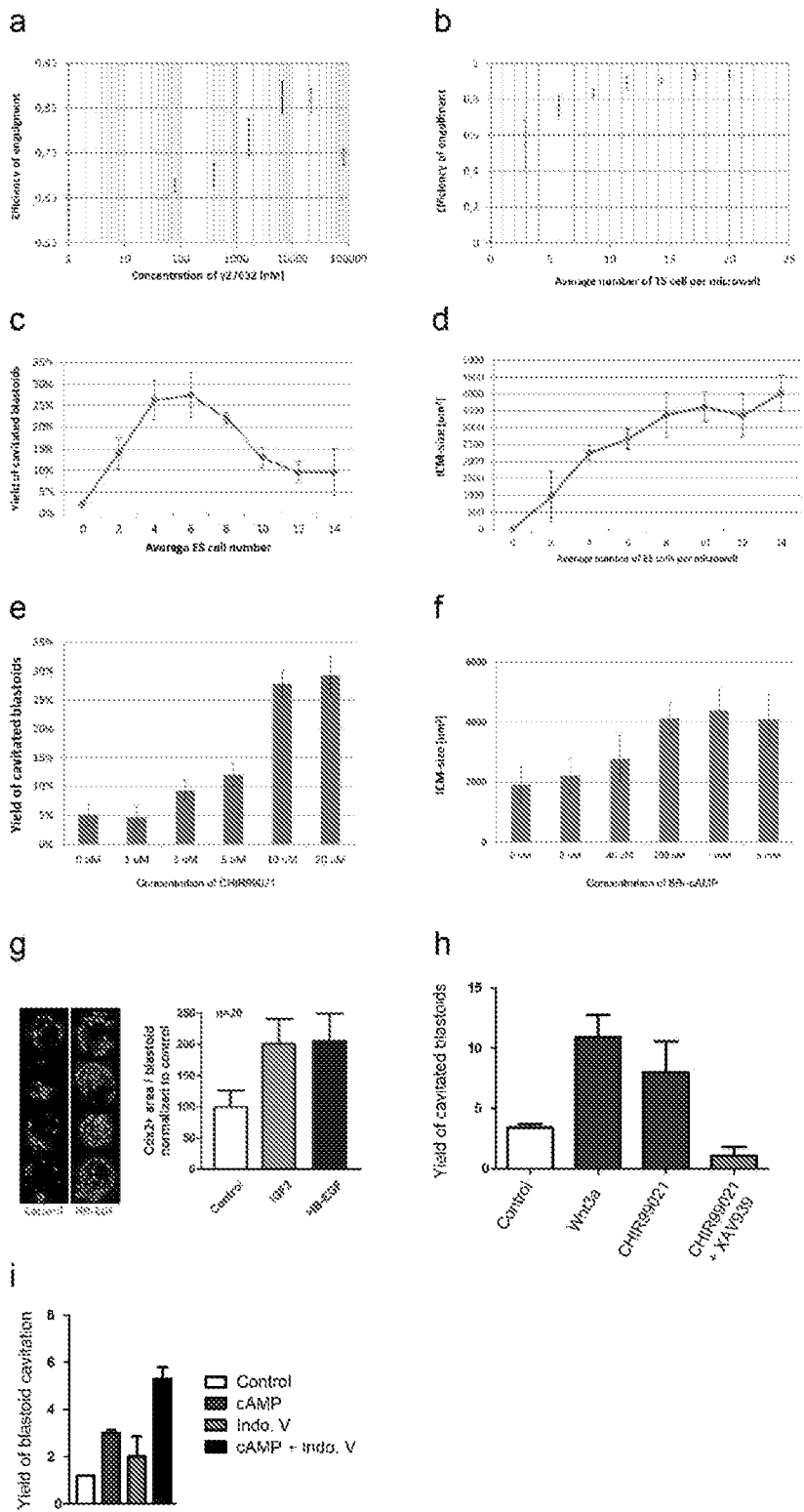
FIG. 4: determination of optimal conditions for formation of an artificial blastocyst.

The size of the inner cell mass (ICM) depends on the average number of ES-cells seeded, and increases with the number of ES-cells seeded per microwell as described in FIG. 4. The size as defined by its projection area is generally between 1000 and 5000 um$^2$, preferably between 2000 and 4500 um$^2$. The size is conveniently expressed by determining the projection area (in um$^2$) of the ICM through light microscopy.

The size of the inner cell mass (ICM) also depends on the concentration of specific biological factors included into the medium. For example, the size of the ICM depends on the concentration of PKA modulators, for example on the concentration of cAMP. The size of the ICM also depends on the concentration of Akt modulators, for example on the concentration of IGF2. The size of the ICM also depends on the concentration of STAT modulators, for example on the concentration of Il6, LIF or Il11.

Further alternatively, the Wnt-pathway, the PKC pathway, the PKA, the MAPK pathway, the Hippo pathway, the Transforming growth factor (Tgf) pathway and the Akt pathway can be modulated by genetic activation as is known in the art.

Thus, in a method according to the present invention, culturing the cell aggregate to obtain a blastoid is done in a cell culture medium, preferably comprising at least one and preferably more of the group consisting of the Wnt-pathway, the PKC pathway, the PKA, pathway, the MAPK pathway, the STAT pathway, the Akt pathway, the Tgf pathway and the Hippo pathway modulators. In a preferred embodiment, one or more of these components are added to a known cell culture medium, such as for instance B27N2, TX or E8 medium.

To obtain an ES-TS cell cluster, it is highly preferred if the ES cells are first seeded onto a microwell array in ES medium including Leukemia Inhibitory Factor (optimally 9 ES cells/microwell). ES cells are cultured for 24 hours and form an aggregate. TS cells are then seeded onto the same microwell array in B27N2 medium (optimally 17 TS cells/microwell). It is highly preferred that an inhibitor of the Rho/ROCK pathway and cytoskeletal tension is added in order to facilitate the aggregation of the TS cells onto the aggregate of ES cells and the formation of a double-layered aggregate. This can be for example an inhibitor of p160ROCK, for example the molecule Y27632, for example at approximately 1-100 µM, preferably around 20 µM.

To obtain a blastoid, the cell aggregate should form an internal cavity. A much preferred means of achieving this is by activating the Wnt signalling pathway, the PKC pathway and the PKA pathway.

This can preferably be achieved by adding a GSK3 inhibitor and/or a Wnt protein to the medium. This more preferably achieved by adding the GSK3 inhibitor CHIR99021 to the medium, preferably at 0.3-30 µM, even more preferably at 3 uM. Also, it is preferred to add the PKA activator 8Br-cAMP to the medium, preferably at 0.1-10 mM, more preferably at 1 mM, the PKC modulator Indolactam V to the medium, preferably at 0.1-10 uM, more preferably at 1 uM.

The formation of a cavity is assessed by the formation of a volume within the aggregate that is not occupied by cellular nucleus. The formation of a cavity is preferably assessed using the cross-sectional section of a cellular aggregate stained with a nuclear-specific dye (for example DAPI). The formation of a cavity is more preferably assessed by the presence of a surface, within the cross-section of a cellular aggregate, which does not contain cellular nucleus and covers more then 5% of the total surface area of the cellular aggregate.

To obtain a blastoid, it is highly preferred if during cavitation, the toti- or pluripotency of at least a subset of the inner cells of the layered cell aggregate which descend from the at least one pluripotent stem cell and have the potential to form an embryo cells is maintained. This can be achieved by modulating the MAPK, STAT, Akt, Tgf and/or Hippo pathways, preferably by activation of the MAPK, STAT, Akt, Tgf pathways and by inhibition of the Hippo pathway.

This is more preferably achieved by adding the MAPK pathway modulator FGF4 ligand to the medium, preferably at 1-150 ng/ml, more preferably at 15 ng/ml, and/or by adding the STAT pathway modulator HB-EGF ligand to the medium, preferably at 5-500 ng/ml, more preferably at 50 ng/ml, and/or by adding the Tgf pathway modulator Tgfb ligand to the medium, preferably at 0.5-50 ng/ml, more preferably at 5 ng/ml, and/or by adding the Akt pathway modulator IGF2 ligand to the medium, preferably at 1-100 ng/ml, more preferably at 10 ng/ml and/or by adding the STAT pathway modulator Il6 ligand to the medium, preferably at 3-3000 ng/ml, more preferably at 300 ng/ml.

The maintenance of the pluripotency of the ICM is assessed by the expression of the transcription factors Octamer-binding transcription factor 4 (Oct4) also known as POU5F1 (POU domain, class 5, transcription factor 1), sex determining region Y-box 2 (Sox2), and Nanog. The expression of these transcription factors is assessed by Polymerase Chain Reaction and/or immunocytochemistry as known in the art.

The levels of expression of the transcription factor must be no more then 5 folds up-regulated or down regulated as compared to embryonic stem cells cultured on polystyrene plates, as known in the art. The expression of these transcription factors can also be assessed by immunohistochemistry. The maximum intensity of a fluorescent antibody specific for the transcription factor must be located within the nucleus and must be no more then 5 fold up-regulated or down regulated as compared to embryonic stem cells cultured on top of a layer of Embryonic Fibroblasts cells seeded on polystyrene plates, as known in the art.

Preferably, both a Wnt modulator and a MAPK modulator are present in the culture medium. The presence of both types of modulators has the advantageous effect of inducing cavitation while maintaining the viability and the pluripotency of the cells.

More preferably, this combination of a Wnt and a MAPK modulators is expanded with the presence of a PKA and a Tgfb modulator. The effect of adding this modulator is increasing the cavitation and the maintenance of the viability and the pluripotency of the trophectoderm and of the ICM.

Even more preferably, the above combination of Wnt, MAPK, PKA and Tgfb modulators is expanded with the presence of Akt, STAT and PKC modulators. This has the beneficial effect of increasing the pluripotency and the viability of the cells.

In a preferred embodiment, culturing a cell aggregate to obtain a blastoid is done in a culture medium comprising a Wnt pathway activator, a MAPK pathway activator, a PKA pathway activator, a PKC pathway modulator, a Tgf pathway activator, an Akt pathway activator, a STAT pathway activator and a Hippo inhibitor.

In a much preferred embodiment, culturing to obtain a blastoid is done in a B27N2 culture medium additionally comprising Y27632, CHIR99021, FGF4, 8Br-cAMP, TGFb1, IGF2, Indolactam V, Il6 and Estradiol. More preferably, in this culture medium Y27632 is present at approximately 1-100 uM, preferably about 20 uM, CHIR99021 is present at approximately 1-25 µM, preferably 3 µM, FGF4 is present at approximately 2-50 ng/ml, preferably about 15 ng/ml, 8Br-cAMP is present at 0.1-10 mM, preferably about 1 mM, TGFb1 is present at approximately 1-15 ng/ml, preferably about 5 ng/ml, IGF2 is present at at 1-15 ng/ml, preferably about 5 ng/ml, Indolactam V is present at 0.1-10 uM, preferably about 1 uM, Il6 is present at 50-900 ng/ml, preferably about 300 ng/ml and Estradiol is present at 1-50 ng/ml, preferably about 10 ng/ml.

It is known that some compounds fall in two or more of the classes mentioned; in that case, use of a single compound with functionality in two or more classes may substitute for the use of separate compounds in each of the classes to which the single compound may be assigned.

In addition to the above it is advantageous to include other compounds to the culture medium, such as a serum, for example fetal bovine serum (FBS), minerals, vitamins, and other compounds that aid in keeping cells in culture alive, proliferating and differentiating.

An example of a preferred culture medium for forming a cell aggregate, that at the time of writing was known as the best mode to practice the invention when culturing a cell aggregate comprising ES-cells and TS-cells, comprises B27N2 medium as defined above, supplemented with (as approximate final concentrations):

20 uM Y27632
3 uM CHIR99021
10 ng/ml IGF2
1 mM 8Br-cAMP
5 ng/ml TGFb1
15 ng/ml FGF4
1 nM 007-AM
1 uM Indolactam V
300 ng/ml Il6
10% fetal bovine serum (FBS)

The invention also pertains to a blastoid which can be obtained by following the present method.

The invention also pertains to a blastoid, such as an artificial blastocyst, which can be obtained by following the present method.

The invention also pertains to an at least double layered cell aggregate which can be obtained by following the present method, preferably a double layered cell aggregate, most preferably an ES-TS cell cluster as described above.

A further advantage of using a culture medium inducing cavitation, epithelisation and maintenance of pluripotency according to the present invention is that a large variety of ES and TS cell lines including or not genetic modifications can be used.

Generally, after cavitation, a blastoid according to the invention has formed from the cell aggregate. The initial artificial blastocyst may be isolated, or grown further in vitro or in vivo. Preferably, a blastoid is cultured at least until cavitation is finished. Cavitation can be observed by conventional light microscopy, which allows for determination of the endpoint of cavitation.

Figure 3:
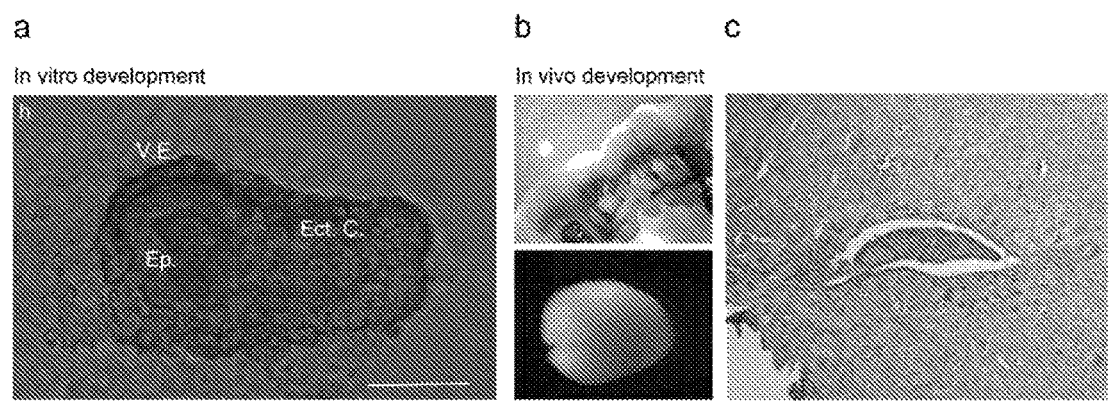
FIG. 3: In vitro and in vivo development of a blastoid. (all scale bars are 500 μm.)

After obtaining the artificial blastocyst, this can be further cultured in vitro to other blastoid stages. Preferably, this is achieved by transferring the cell culture to an adherent surface as is known in the art (see *Development of Mouse Embryos in vitro: Preimplantation to the Limb Bud Stage* Author(s): L. T. Chen and Y. C. HsuReviewed work(s): Source: *Science*, New Series, Vol. 218, No. 4567 (Oct. 1, 1982), pp. 66-68), which is incorporated herein in its entirety. After cavitation of a blastoid has finished, the artificial blastocyst can be cultured for as long as the cells can be kept alive (see FIG. 3).

As a second option, an artificial blastocyst or any immediately previous or further developed blastoid stage can be grown further in vivo by placing the blastocyst in the infidibulum and/or the uterus of a mammal, preferably the uterus of a mammal of the same or similar species the blastocyst' cells derive from. This is achieved as conventionally known in the art (see: *Manipulating the Mouse Embryo: A Laboratory Manual (Third Edition)*. Andras Nagy, Samuel Lunenfeld Research Institute; Marina Gertsenstein, Samuel Lunenfeld Research Institute; Kristina Vintersten, European Molecular Biology Laboratory; Richard Behringer, University of Texas M.D. Anderson Cancer Center, Cold spring harbour laboratory press). This method is preferred if growing of the blastoid into a foetus or into a live animal is intended (see FIG. 3).

It is also possible however for transferring the cellular aggregate prior to its cavitation, i.e. as an (at least) double layered cell aggregate which can cavitate inside the uterus.

It is also possible however for in vivo growing of a blastoid according to the invention, to implant the blastoid only after some further in vitro development. Therefore, implantation into a uterus as a gastrula, epiblast or foetus is possible, also, which means that in general, culturing of the artificial blastocyst in vitro is continued for about 1 to 30 days after formation, more preferably 1-10 days before implantation into a uterus. Any of the options involving placing the artificial blastocyst or a further-developed in vitro grown blastoid or foetus obtained therefrom into a uterus to allow further in vivo growth in the context of the present invention is called in vivo growing of a blastoid.

Live mammals obtained by growing blastoids in vivo can have genetic modifications. This can conveniently be achieved by genetically modifying a cell used to form the cell aggregate, as described above. One genetic modification of a cell can be multiplied by expanding such cells as is known to obtain a single cell line with the same genetic profile, and the same genetic modification.

Alternatively, live chimeras can be obtained by forming a cell aggregate from cell lines with different genetic profiles, such as for example chimeras stemming from cell lines from different species, or chimeras from cell lines with different genetic modifications. Preferably however for forming a cell aggregate, the different genetic profiles stem from one or more genetic variations, including genetic modifications, of cells of the same species, to result a live chimera with two or more genetic variations within the same species.

Creating several cell lines with different genetic modifications from one originally derived cell line results in a genetic library with the same "base" genetic profile but with different genetic modifications, as is understood by the skilled person. Such cell lines can in the context of the present invention lead to either genetically uniform or to genetically varied libraries of blastoids, foetuses or live mammals. Thus, the present invention allows a convenient route to genetically modified mammals, without the requirement of subsequent breeding and crossing of chimeras. At the same time, high genetic homogeneity, or controlled genetic variation within one genetic profile can be obtained.

Regenerative medicine aims at replacing or regenerating tissues or organs following a disease or a trauma. Later, during adult life, tissue regeneration can be achieved via a transient reconstitution of the embryonic program. Therefore, in vitro blastoid provides easy access to the mechanisms or regeneration and to the required tissue or to cells with the correct differentiation capability. This is achieved without the use of live animals for the harvesting of embryos. Blastoids according to the present invention can thus be used to obtain suitably differentiated tissue for use in regenerative medicine by culturing the blastoid until cells with the right differentiation capacity have formed. Such cells may be extracted and implanted into live tissue with the aim of repairing this tissue. Especially in case the blastoid is derived from cells of the same genetic background as the tissue to be repaired, such as by using induced pluripotent stem cells obtained from the same individual, this approach results in genetically equal cells capable of repairing a tissue that requires repairing.

The recreation of the microenvironmental niche of pluripotent stem cells via their encapsulation in a blastoid may induce genetic and/or epigenetic changes resulting in preferential properties over current culture of stem cells, such as the enhanced ability to perform genetic editing (e.g. homologous recombination).

In the field of toxicology, predicting the embryonic toxicity of a test substance is done by the European Center for the Validation of Alternative Methods (ECVAM) by the use of the embryonic stem cell test (EST). This assay makes use of the differentiation of mouse embryonic stem cells into cardiomyocites in vitro. An in vitro generated artificial blastocyst, or a tissue, embryo or foetus grown from it, provides a valuable, complementary model for such toxicity tests.

In the field of drug development, the efficacy and safety of preclinical drug discovery is hampered by a lack of relevant in vitro models. Candidate drugs are routinely tested on monolayers of cells which only poorly reflect the physiological context of a tissue. Complex in vitro models of live tissue are of high importance to mimic the patho-physiologies of diseases. Thus, the present method for obtaining a blastoid bears high promise for identifying novel drug targets and enhances the probability of clinical success of new drugs.

In addition, clinical drug testing often requires "knock-out" animals, in which certain genes have been inactivated or altered to have easy access to animals having the disease under study. With the present invention, large amounts of animals used for such study may be grown, either genetically uniform or with controlled genetic modifications as described. This facilitates the testing of new drugs on animal models, and allows for higher statistical relevance.

In the field of genetic diseases, genetically altered animals are used to identify potential treatments. As explained above, such animals are readily obtained by the present method, without sacrificing many mother animals, and without the requirement of creating and further crossing and breeding of chimeras.

Also, genetic defects of unknown origin may now be multiplied by harvesting a single cell, and by subsequent in vitro expansion to a cell line suitable for forming an aggregate according to the present invention. Thus, a multitude of animals with the genetic defect under study may be obtained, without further genetic variation as is customary when genetic defects are procreated biologically.

The invention will be further illustrated by means of the following, non-restrictive examples.

EXAMPLES

Compounds and Abbreviations

B27N2 medium=a cell culture medium known in the art, the composition of which is described above.

E8 medium=a cell culture medium available commercially, the composition of which is described in *Nat. Methods.* 2011, *"Chemically defined conditions for human iPSC derivation and culture"* Chen G$^1$, Gulbranson D R, Hou Z, Bolin J M, Ruotti V, Probasco M D, Smuga-Otto K, Howden S E, Diol N R, Propson N E, Wagner R, Lee G O, Antosiewicz-Bourget J, Teng J M Thomson J A.

TX medium=a cell culture medium, the composition of which is described in Kubaczka C, Senner C, Araúzo-Bravo M J, Sharma N, Kuckenberg P, Becker A, Zimmer A, Brüsle O, Peitz M, Hemberger M, Schorle H *Derivation and Maintenance of Murine Trophoblast Stem Cells under Defined Conditions. Stem Cell Reports.* 2014 Jan. 30; 2(2)232-42 doi: 10.1016/j.stemcr.2013 12.013.eCollection 2014 Feb. 11.

ES medium=a cell culture medium available commercially, the composition of which is described above.

CHIR99021=a compound that inhibits GSK3a and GSK3@ with chemical name 6-{2-[4-(2,4-dichlorophenyl)-5-(4-methyl-1H-imidazol-2-yl)-pyrimidin-2-ylamino]-ethylamino}-nicotinonitrile (CAS 252917-06-9).

LIF: Leukemia Inhibition Factor is a protein and a growth factor known in the art to maintain the pluripotency of mouse and rat embryionic stem cells Y27632=(1R,4r)-4-((R)-1-aminoethyl)-N-(pyridin-4-yl) cyclohexanecarboxamide. A molecule known in the art to inhibit the Rho/ROCK pathway (CAS 146986-50-7).

Activin=a protein and a growth factor known in the art to activate the TGF signalling pathway Transforming growth factor Beta 1 (TGFb1)=a protein and a growth factor known in the art to activate the TGF signalling pathway Indolactam V=A molecule known in the art to modulate the PKC pathway (90365-57-4)

Il6=a protein and a growth factor known in the art to activate the STAT signalling pathway.

Fibroblast Growth Factor 4 (FGF4)=a protein and a growth factor known in the art to activate the MAPK signalling pathway Heparin-Binding EGF-like Growth factor (HB-EGF)=a protein and a growth factor known in the art to activate the MAPK signalling pathway Insulin-like growth factor 2 (IGF2)=a protein and a growth factor known in the art to activate the Akt pathway Insulin=a protein and an hormone known in the art to activate the AKT signalling pathway 17β-estradiol=a hormone known in the art to modulate the Hippo pathway via the estrogen receptor and GPR30 (CAS 79037-37-9)

Tamoxifen=a molecule known in the art to modulate the Hippo pathway via the estrogen receptor and GPR30 (CAS 10540-29-1)

G-1=a molecule known in the art to modulate the Hippo pathway via GPR30 (CAS 881639-98-1)

ES-Medium Contained:
- Pen/Strep 50 µg/ml (an antibiotic that can be obtained from Invitrogen, catalog number 15070-063)
- L-glutamine 1 mM
- 5 ml Non Essential Amino Acids (Invitrogen #11140-035, ×100)
- beta-mercaptoethanol 0.1 mM
- 75 ml (=15%) FBS
- DMEM to 500 ml
- Leukemia Inhibitory Factor, 500-1000 Units/ml The "2i" medium used comprised ES-medium described above, with the following added components:
- 1 µM PD0325901 CAS Number 391210-10-9.
- 3 µM CHIR99021 CAS Number 252917-06-9.

TS-Medium Contained:
- 250 ml of RPMI medium 1640 (Invitrogen 61870 or 11875)
- 65 ml of Foetal Bovine serum
- Pen/Strep, 50 µg/ml
- Sodium Pyruvate 1 mM
- L-Glutamine, 2 mM
- beta-mercaptoethanol 0.1 mM
- FGF-4, 25 ng/ml
- Heparin, 1 µg/ml The B27N2 Medium
- 234 ml DMEM/F12 (Invitrogen #11320-074, [−] L-Glutamine)
- 234 ml Neurobasal (Invitrogen #21103-049, [+] L-Glutamine)
- 2.5 ml (−1 mM) L-Glutamine (Invitrogen #25030, ×100)
- 5 ml Non Essential Amino Acids (Invitrogen #11140-035, ×100)
- 5 ml Pen/Strep (Invitrogen #15140)
- 5 mg/ml BSA (Sigma)
- 5 ml Sodium Pyruvate, final concentration 1 mM (Invitrogen #11360-039, ×100)
- 2.3 µl (=0.1 mM) beta-Mercaptoethanol (Sigma)
- 5 ml N2 supplement (Invitrogen)
- 10 ml B27 supplement (Invitrogen)

Preparation of a Culture Medium for Blastoid Formation:
Stock solutions to supply preferred components to the culture medium were:
- 10% FBS (Greiner Bio one)
- Y27632: 20 µM
- CHIR99021 (Axon Medchem, axon 1386). 3 uM
- 8Br-cAMP (8Br-cAMP Economy grade, Biolog, B007-50E). 1 mM.
- 007-AM (Biolog C051). 1 nM.
- IGF2 (R&D system, 292-G2-050) 10 ng/ml
- TGFb1 (R&D system 338-AC-010), 10 ng/ml
- FGF4 (R&D system 235-F4-025), 15 ng/ml
- HB-EGF (R&D system 259-HE-050), 50 ng/ml
- 17β Estradiol (491187 Aldrich), 10 ng/ml
- Indolactam V (3651 Tocris), 1 uM

Example 1: Obtaining a Blastoid

Day −4
Mouse embryonic fibroblast (EF)-cells were seeded at 15.000 cells/cm$^2$ in tissue-culture polystyrene plates in ES-medium. The cells were allowed to grow for one day in an incubator set at 37° Celsius.

Day −3
Mouse ES-cells were seeded on the layer of mouse EF at 15.000 cells/cm$^2$ in "2i" medium containing LIF (500 Units/ml). The mouse ES-cells were cultured for two days in an incubator set at 37° Celsius.

Day −2
Mouse TS-cells were seeded on a layer of mouse EF-cells at a density of 10000 cells/cm$^2$ in TS-medium in an incubator set at 37 Celsius degrees.

Day −1
Mouse ES-cells were trypsinized, and the mouse EF-cells were depleted by incubating 2×20 minutes in one 15 cm dish using 4 ml of ES medium.

Mouse ES-cells were seeded at 7 cells/microwell in 150 µL ES medium. The ES-cells were allowed to settle for 20 minutes, after which 1 ml of ES medium was added, and the culture was placed in an incubator at 37° Celsius for one day to allow the mouse ES-cells to cluster.

Day 0
The mouse TS cell culture obtained as described for day −2 was trypsinized, and the mouse EF-cells were depleted by incubating 2×20 minutes in one 15 cm dish using 4 ml of TS medium. The obtained mouse TS cells were resuspended in B27N2 medium.

Mouse TS-cells were seeded at 17 cells/microwell in 150 µL B27N2 medium. After 20 minutes, 1 ml of B27N2 medium was added that included 10% FBS, Y27632 20 µM, 8Br-cAMP (1 mM), 007-AM (1 nM) and CHIR 3 µM, FGF4 15 ng/ml, Tgfb1 5 ng/ml, IGF2, 10 ng/ml, estradiol 10 ng/ml. The cells were placed in an incubator set at 37° Celsius to form the ES-TS cell cluster.

Over the next days, the following components were added so as to achieve the indicated final concentration, assuming a zero initial concentration despite a possible remnant presence of these compounds.

Day 3 (65 hours)
The B27N2 medium is renewed to which is added
- FGF4 (15 ng/ml)
- TGFb1 (5 ng/ml)

The 12-well plate with the agarose chips was taken out of the incubator after about 110 hours. By now, artificial blastocysts had formed by cavitation of the ES-TS cell cluster. At this point, the non-adherent scaffold can be replaced by an adhering scaffold (e.g. polystyrene tissue culture plate), to continue growing the blastoid in vitro or the blastoid can be transferred to the uterus of a pseudo-pregnant mouse.

Example 2: Visualization

Double layer formation: the formation of an (at least) double layered cell aggregate with an external layer of TS cells and an inner layer of ES cells is evaluated using transgenic cell lines. Specifically, ES cells were transfected with Histone 2B and a Red Fluorescent Protein under the control of a cytomegalovirus promoter and clonally derived. The H2B-RFP ES cells are thus constitutively expressing a red fluorescence within their nucleus which allows for their tracking.

TS cells were derived from a mouse constitutively expressing Green Fluorescent Protein (GFP) under the control of a cytomegalovirus promoter in all cells. The GFP TS cells are thus expressing a green fluorescence in their cytoplasma which allows for their tracking.

The formation of a double-layered aggregate is thus assessed by observing a green outer layer of cells and a red inner layer of cells. The efficiency of engulfment is determined as the percentage of green-colored projection area (representing the TS cell layer) that overlaps with an artificial 3-pixel-wide ring drawn around the red-colored projection area (representing the inner aggregate of ES cells) after 24 hours of culturing the ES-TS cell clusters. The said efficiency of engulfment described in FIG. 4 represents the average value taken from approximately 200 ES-TS cell clusters.

Cavitation: The formation of a cavity is assessed by the formation of a volume within the aggregate that is not occupied by cellular nucleus. The formation of a cavity is preferably assessed using the cross-sectional section of a cellular aggregate stained with a nuclear-specific dye (for example DAPI). The formation of a cavity is more preferably assessed by the presence of a surface within the cross-section of a cellular aggregate that does not contain cellular nucleus and covers more then 20% of the total surface area of the cellular aggregate.

CDX2, Oct4, Nanog expression: The expression of the transcription factor CDX2 is assessed by conventional immunocytochemistry in ES-TS aggregates including GFP-expressing TS cells. The expression of cdx2 is assessed as the number of GFP positive cells with a cdx2 positive nucleus per 10 μm microscopic section. The expression of the transcription factors Oct4 and Nanog is assessed by conventional immunocytochemistry in ES-TS aggregates including H2B-RFP expressing ES cells. The expression of Oct4 and Nanog is assessed as the number of H2B-RFP positive cells with an Oct4 or Nanog positive nucleus per 10 μm microscopic section.

Pictoral Summary of the Procedure for Blastoid Formation:

Free suspended multipotent mouse ES-cells are inserted in 200 μm microwells located in an agarose chip that is placed in a 12-well plate (FIG. 1a), and allowed to cluster in ES culture medium. To these clusters, free suspended mouse TS-cells are added (FIG. 1b), as well as culture medium. Under the influence of the described compounds in the culture medium, among which a Rho/ROCK inhibitor, the cells form a double layered aggregate of trophoblast stem cells (FIG. 1c, green) and embryonic stem cells (FIG. 1c, red) which then, under the influence of among others a Wnt pathway modulator, a PKA pathway modulator and a PKC pathway modulator present in the culture medium cavitates and forms a trophectoderm (d, green) and a distinct inner cell mass (FIG. 1d, red) to result in a blastoid.

Figure 2:
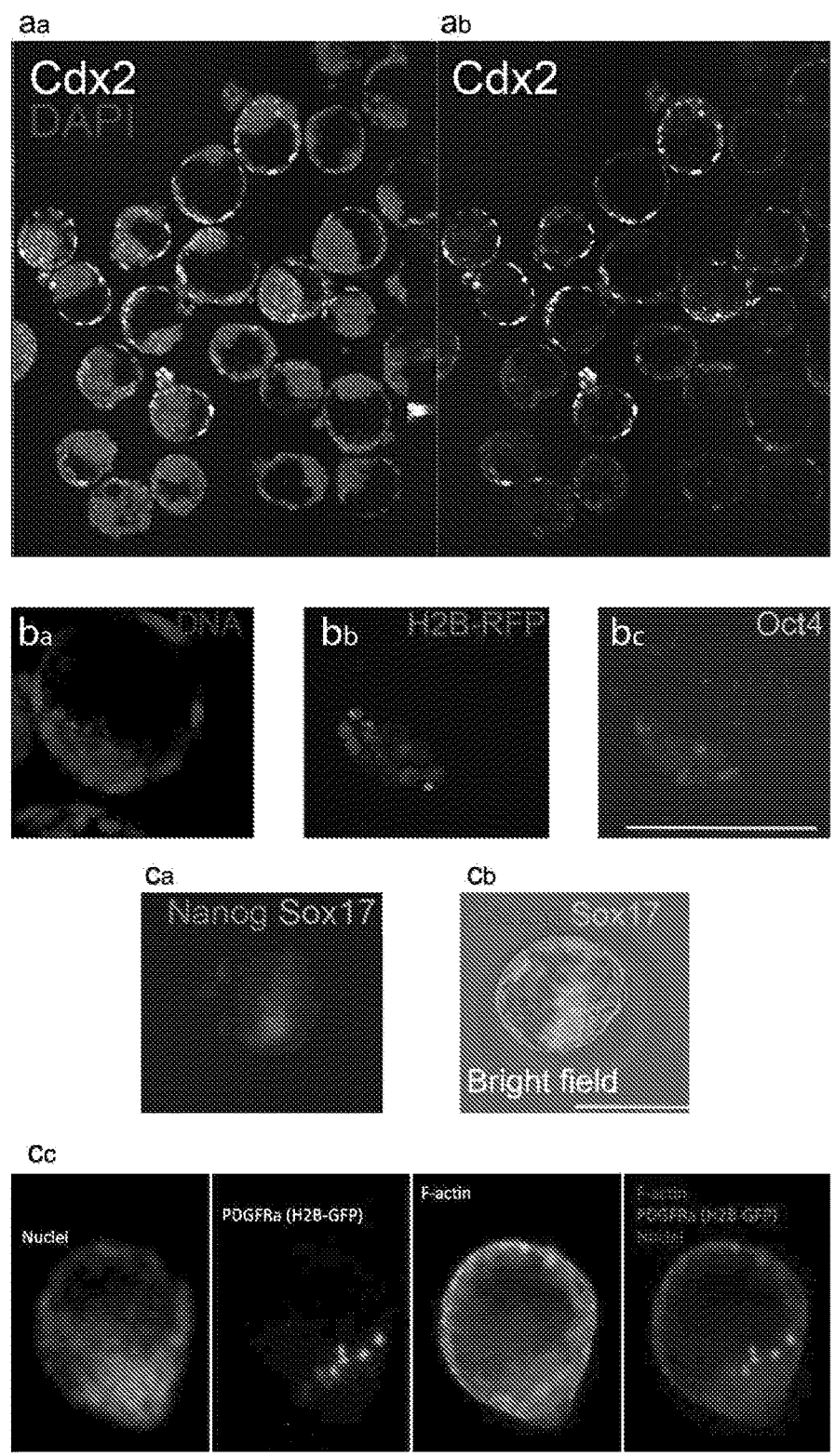
FIG. 2: Molecular characterization of a blastoid. (all scale bars are 200 μm.)

The trophectoderm maintains pluripotency as observed by CDX2 expression in trophoblast stem cells (FIG. 2a) by inclusion of a MAPK pathway activator, a STAT pathway activator, an Akt pathway activator, a Tgf pathway activator and a Hippo pathway inhibitor. The inner cell mass maintains pluripotency as observed by Oct4 expression in H2B-RFP labelled embryonic stem cells (FIG. 2b). The inner cell mass separates into an epiblast and a primitive endoderm as seen by Nanog, Sox17 and PDGFRa expression (FIG. 2c).

Upon adhesion to an adhering scaffold, the blastoid further develops by extension of the Epiblast (Ep.), the formation of a Visceral Endoderm (V.E.) and the formation of an Ectoplacental cone (Ect. C.), in similarity to a naturally-formed blastocyst (FIG. 3a).

Upon transfer into an uterus (FIG. 3b), the blastoids induce the formation of deciduae (FIG. 3c) in which they further develop (FIG. 3d), into a fetus or a live animal.

CONCLUSION

Upon combination of in vitro expanded mouse ES-cells and mouse TS-cells from cell lines in a culture medium preferably comprising one or more from the group of a Rho/ROCK signalling modulator, Wnt signalling modulator, a PKA signalling modulator, a PKC signalling modulator, a MAPK signalling modulator, a STAT signalling modulator, an Akt signalling modulator, a Tgf signalling modulator, a Hippo signalling modulator and an EPAC 1 signalling activator, ES-cells and TS-cells combine into an ES-TS cell cluster, that after about 110 hours displays cavitation, epithelisation, maintenance of pluripotency and differentiation of a primitive endoderm. Thus, a blastoid is formed.

The artificial blastocyst can be isolated and optionally fixated or implanted into a uterus. Also, it can be further cultured in vitro to result in a further developed blastoid. This also can be isolated and optionally fixated, but it may also be implanted into a uterus for further in vivo growing.

The invention claimed is:

1. An in vitro method of making an at least double layered mouse cell aggregate, the method comprising:
   seeding between 2 and 14 mouse embryonic stem (ES) cells into a flat-bottom microwell with a diameter of between 100 and 500 micrometers;
   culturing the ES cells in a first culture medium to form an aggregate;
   seeding between 3 and 20 mouse trophoblast stem (TS) cells into the microwell in a second culture medium; and
   culturing the mixture of ES and TS cells to obtain an at least double layered cell aggregate.

2. The method according to claim 1, wherein the embryonic stem cells and/or trophoblast stem cells are obtained from a cell line.

3. The method according to claim 1, wherein the microwell has a non-adherent surface.

4. The method according to claim 1, wherein the first and/or second culture medium comprises a Rho/ROCK inhibitor.

5. The method according to claim 1, wherein the first and/or second culture medium comprises a modulator of a pathway selected from the group consisting of the Writ-pathway, the PKA pathway, the PKC pathway, the MAPK pathway, the STAT pathway, the Akt pathway, the Tgf pathway and the Hippo pathway.

6. The method according to claim 5, wherein the modulator of the Wnt-pathway is an activator of the Wnt-pathway.

7. The method according to claim 6, wherein the activator of the Wnt-pathway is a glycogen synthase kinase inhibitor or a Wnt agonist.

8. The method according to claim 5, wherein the modulator of the PKA pathway is an activator of the PKA pathway.

9. An at least double layered cell aggregate obtained by the method according to claim 1.

\* \* \* \* \*

UNITED STATES PATENT AND TRADEMARK OFFICE
CERTIFICATE OF CORRECTION

PATENT NO. : 9,822,336 B2
APPLICATION NO. : 14/784659
DATED : November 21, 2017
INVENTOR(S) : Nicolas Clément Rivron et al.

Page 1 of 1

It is certified that error appears in the above-identified patent and that said Letters Patent is hereby corrected as shown below:

In the Specification

| | | |
|---|---|---|
| Column 11, | Line 30, | change "Galas, T G., Durning," to --Golos, T G., Durning,-- |
| Column 17, | Line 59, | change "Vrij E S, Rouwkema" to --Vrij E J, Rouwkema-- |
| Column 18, | Line 64, | change "of GSK-3@ from" to --of GSK-3β from-- |
| Column 18, | Line 66, | change "@-catenin and" to --β-catenin and-- |
| Column 20, | Line 22, | change "(e.g. Ras, Rap 1)." to --(e.g. Ras, Rap1).-- |
| Column 22, | Line 62, | change "is asset via the" to --is assessed via the-- |
| Column 25, | Line 22, | change "Dobie B, Woodgett" to --Doble B, Woodgett-- |
| Column 25, | Line 52, | change "Takata I V, Tokoro" to --Takata N, Tokoro-- |
| Column 26, | Line 17, | change "(7190'519-23. The" to --(7194): 519-23. The-- |
| Column 26, | Line 19, | change "Dobie B, Woodgett" to --Doble B, Woodgett-- |
| Column 34, | Line 26, | change "Brüsle O, Peitz M," to --Brüstle O, Peitz M,-- |
| Column 34, | Line 34, | change "GSK3@ with" to --GSK3β with-- |
| Column 38, | Line 13, | change "and an EPAC 1" to --and an EPAC1-- |

In the Claims

| | | | |
|---|---|---|---|
| Claim 5, | Column 38, | Lines 46,47 | change "of the Writ-pathway," to --of the Wnt-pathway,-- |

Signed and Sealed this
Twelfth Day of June, 2018

Andrei Iancu
*Director of the United States Patent and Trademark Office*